US010137452B2

(12) United States Patent
Conner et al.

(10) Patent No.: US 10,137,452 B2
(45) **Date of Patent: *Nov. 27, 2018**

(54) THERMAL UNIFORMITY FOR THERMAL CYCLER INSTRUMENTATION USING DYNAMIC CONTROL

(71) Applicant: LIFE TECHNOLOGIES CORPORATION, Carlsbad, CA (US)

(72) Inventors: Thomas Conner, Mountain View, CA (US); Chee Kiong Lim, Singapore (SG); Michael Pallas, San Bruno, CA (US); Chee Wee Ching, Johor Bahru (MY)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/410,708

(22) Filed: Jan. 19, 2017

(65) Prior Publication Data

US 2017/0225169 A1 Aug. 10, 2017

Related U.S. Application Data

(63) Continuation of application No. 13/082,888, filed on Apr. 8, 2011, now Pat. No. 9,566,583.

(60) Provisional application No. 61/322,529, filed on Apr. 9, 2010.

(51) Int. Cl.

| | |
|---|---|
| ***B01L 7/00*** | (2006.01) |
| ***C12M 1/40*** | (2006.01) |
| ***C12Q 3/00*** | (2006.01) |

(52) U.S. Cl.

CPC ........... *B01L 7/52* (2013.01); *B01L 2200/147* (2013.01); *B01L 2300/1822* (2013.01); *B01L 2300/1894* (2013.01)

(58) Field of Classification Search

CPC ............................ B01L 7/52; B01L 2200/147

See application file for complete search history.

(56) References Cited

U.S. PATENT DOCUMENTS

| | | | |
|---|---|---|---|
| 3,036,893 | A | 5/1962 | Natelson |
| 3,128,239 | A | 4/1964 | Page |
| 3,216,804 | A | 11/1965 | Natelson |
| 3,260,413 | A | 7/1966 | Natelson |
| 3,261,668 | A | 7/1966 | Natelson |
| 3,271,112 | A | 9/1966 | William et al. |
| 3,331,665 | A | 7/1967 | Natelson |
| 3,368,872 | A | 2/1968 | Natelson |
| 3,556,731 | A | 1/1971 | Martin |
| 4,865,986 | A | 9/1989 | Coy et al. |
| 4,950,608 | A | 8/1990 | Kishimoto |
| 5,038,852 | A | 8/1991 | Johnson et al. |
| 5,061,630 | A | 10/1991 | Knopf et al. |
| 5,224,536 | A | 7/1993 | Eigen et al. |
| 5,333,675 | A | 8/1994 | Mullis et al. |
| 5,430,957 | A | 7/1995 | Eigen et al. |
| 5,441,576 | A | 8/1995 | Bierschenk et al. |
| 5,475,610 | A | 12/1995 | Atwood et al. |
| 5,504,007 | A | 4/1996 | Haynes |
| 5,525,300 | A | 6/1996 | Danssaert et al. |
| 5,601,141 | A | 2/1997 | Gordon et al. |
| 5,602,756 | A | 2/1997 | Atwood |
| 5,656,493 | A | 8/1997 | Mullis et al. |
| 5,716,842 | A | 2/1998 | Baier et al. |
| 5,802,856 | A | 9/1998 | Schaper et al. |
| 5,819,842 | A | 10/1998 | Potter et al. |
| 5,871,908 | A | 2/1999 | Henco et al. |
| 6,015,534 | A | 1/2000 | Atwood |
| 6,093,370 | A | 7/2000 | Yasuda et al. |
| 6,106,784 | A | 8/2000 | Lund et al. |
| 6,525,550 | B2 | 2/2003 | Pan |
| 6,558,947 | B1 | 5/2003 | Lund |
| 6,633,785 | B1 | 10/2003 | Kasahara et al. |
| 6,767,512 | B1 | 7/2004 | Lurz et al. |

(Continued)

FOREIGN PATENT DOCUMENTS

| | | |
|---|---|---|
| CN | 102483642 | 12/2014 |
| CN | 103003448 | 6/2015 |

(Continued)

OTHER PUBLICATIONS

"Cooling Machine CPU Cooler, Thermaltake," printed from http://www.thermaltake.com/coolers.4in1_heatpipe/cl-pO114bigtyphoon/cl-pO114.htm, May 8, 2006, 1-2.

(Continued)

*Primary Examiner* — David C Thomas

(57) ABSTRACT

A method for performing polymerase chain reactions (PCR) for improving thermal non-uniformity is provided. The method includes measuring a first temperature, by a first sensor, of a first sample block sector of a sample block and measuring a second temperature, by a second sensor, of a second sample block sector of the sample block that is adjacent to the first sample block sector. The method further includes calculating, by a thermoelectric controller, a difference in temperature between the first temperature and the second temperature and adjusting, by the thermoelectric controller, the first temperature of the first sample block sector based on the difference in temperature by using one or more thermoelectric coolers. The one or more thermoelectric coolers is configured to heat or cool the first sample block sector by adjusting power output from the thermoelectric controller.

20 Claims, 28 Drawing Sheets

(56) References Cited

U.S. PATENT DOCUMENTS

| | | | |
|---|---|---|---|
| 6,814,934 B1 | 11/2004 | Higuchi | |
| 6,825,047 B1 | 11/2004 | Woudenberg et al. | |
| 7,611,674 B2 | 11/2009 | Heimberg et al. | |
| 7,727,479 B2 | 6/2010 | Heimberg et al. | |
| 8,389,288 B2 | 3/2013 | Heimberg et al. | |
| 8,676,383 B2 | 3/2014 | Tan et al. | |
| 8,721,972 B2 | 5/2014 | Heimberg et al. | |
| 9,457,351 B2 | 10/2016 | Tan et al. | |
| 9,566,583 B2 * | 2/2017 | Conner | B01L 7/52 |
| 2001/0001644 A1 | 5/2001 | Coffman et al. | |
| 2002/0001848 A1 | 1/2002 | Bedingham et al. | |
| 2002/0068357 A1 | 6/2002 | Mathies et al. | |
| 2003/0214994 A1 | 11/2003 | Schicke | |
| 2004/0076996 A1 | 4/2004 | Kondo et al. | |
| 2004/0122559 A1 * | 6/2004 | Young | B01L 7/52 700/269 |
| 2004/0241048 A1 | 12/2004 | Shin et al. | |
| 2005/0133724 A1 | 6/2005 | Hsieh | |
| 2006/0001644 A1 | 1/2006 | Arakawa et al. | |
| 2006/0024816 A1 | 2/2006 | Fawcett et al. | |
| 2006/0228268 A1 | 10/2006 | Heimberg et al. | |
| 2008/0026483 A1 | 1/2008 | Oldenburg | |
| 2008/0176292 A1 | 7/2008 | Ugaz et al. | |
| 2008/0116184 A1 | 9/2008 | Lim et al. | |
| 2008/0274511 A1 * | 11/2008 | Tan | B01L 3/50855 435/91.2 |
| 2009/0155765 A1 * | 6/2009 | Atwood | B01L 3/50851 435/3 |
| 2009/0325277 A1 | 12/2009 | Shigeura et al. | |
| 2010/0116896 A1 | 5/2010 | Goemann-Thoss et al. | |
| 2010/0120099 A1 | 5/2010 | Heimberg et al. | |
| 2010/0120100 A1 | 5/2010 | Heimberg et al. | |
| 2013/0157376 A1 | 6/2013 | Nay | |

FOREIGN PATENT DOCUMENTS

| | | |
|---|---|---|
| DE | 1900279 | 9/1969 |
| DE | 1966115 | 5/1998 |
| DE | 102007003754 | 7/2008 |
| EP | 0089383 | 9/1983 |
| EP | 0488769 | 6/1992 |
| EP | 0545736 | 6/1993 |
| EP | 0776967 | 6/1997 |
| EP | 0812621 | 12/1997 |
| WO | 1989/012502 | 12/1989 |
| WO | 1990/005947 | 5/1990 |
| WO | 1992/004979 | 4/1992 |
| WO | 1995/011294 | 4/1995 |
| WO | 1998/020975 | 5/1998 |
| WO | 1998/043740 | 10/1998 |
| WO | 1999/016549 | 4/1999 |
| WO | 2001/024390 | 4/2001 |
| WO | 2004/105947 | 12/2004 |
| WO | 2004/108288 | 12/2004 |
| WO | 2007/146433 | 12/2007 |
| WO | 2008/090914 | 3/2008 |
| WO | 2008/070198 | 6/2008 |
| WO | 2008/116184 | 9/2008 |
| WO | 2009/094061 | 7/2009 |
| WO | 2010/502228 | 11/2010 |
| WO | 2011/124918 | 10/2011 |

OTHER PUBLICATIONS

"CoolerMaster Expand Your Imagination, Hyper 6 (KHC-V81)", printed from http://www.coolermaster.com/index.php?LT=english&language_s=2&url_place=product&pserial=KHC-V81&oth. May 8, 2006, 1-5.

German Patent Office Search Report for DE 29917313.5, dated Sep. 30, 2010.

"LightCycler® 480 System Rapid by Nature—Accurate by Design", *Roche Diagnostics*, printed from www.roche-applied-science.com., Nov. 3, 2009, 16.

Notification of Transmittal of the International Search Report, International Searching Authority, International Application No. PCT/US07/77696, dated Jul. 14, 2008, 9.

"Stratagene", *Quantitative PCR Systems*, May 2006, 1-12.

"Translation of claims of International patent specification WO 98/20975", dated Sep. 30, 2010.

"Translation of portions of German patent specification DE 19646115 A1 ", dated Sep. 30, 2010.

07841931.4, "Extended European Search Report dated May 25, 2011", dated May 25, 2011, 4.

Cheng, J.Y., et al., "Performing Microchannel Temperature Cycling Reactions Using Reciprocating Reagent Shuttling Along a Radial Temperature Gradient", 2005, 931-940.

EP11766806.1, Extended European Search Report for Application No. 11766806.1 dated Nov. 5, 2013, 1-5.

PCT/US2011/031750, International Preliminary Report on Patentability dated Oct. 9, 2012.

PCT/US2011/031750, International Search Report, dated Dec. 26, 2011, pp. 1-6.

PCT/US2015/014357, International Prelliminary Report on Patentability dated Aug. 23, 2016, 11 pgs.

Pogfai, T. et al., "Low Cost and Portable PCR Thermoelectric Cycle", *International Journal of Applied Biomedical Engineering*, vol. 1, No. 1, 2008, 41-45.

* cited by examiner

THERMAL UNIFORMITY FOR THERMAL CYCLER INSTRUMENTATION USING DYNAMIC CONTROL

CROSS-REFERENCE TO RELATED APPLICATIONS

This application is a continuation of U.S. application Ser. No. 13/082,888 filed Apr. 8, 2011, which claims the benefit of priority of U.S. Provisional Application No. 61/322,529, filed Apr. 9, 2010, which is incorporated herein by reference in its entirety.

BACKGROUND

Generally, to amplify DNA (Deoxyribose Nucleic Acid) using the PCR process, it is necessary to cycle a specially constituted liquid reaction mixture through several different temperature incubation periods. The reaction mixture is comprised of various components including the DNA to be amplified and at least two primers sufficiently complementary to the sample DNA to be able to create extension products of the DNA being amplified. A key to PCR is the concept of thermal cycling: alternating steps of melting DNA, annealing short primers to the resulting single strands, and extending those primers to make new copies of double-stranded DNA. In thermal cycling the PCR reaction mixture is repeatedly cycled from high temperatures of around 90° C. for melting the DNA, to lower temperatures of approximately 40° C. to 70° C. for primer annealing and extension. Generally, it is desirable to change the sample temperature to the next temperature in the cycle as rapidly as possible. The chemical reaction has an optimum temperature for each of its stages. Thus, less time spent at non optimum temperature means achieving better chemical results. Also a minimum time for holding the reaction mixture at each incubation temperature is required after each said incubation temperature is reached. These minimum incubation times establish the minimum time it takes to complete a cycle. As such, any transition time between sample incubation temperatures is time added to this minimum cycle time. Since the number of cycles is fairly large, this additional time unnecessarily heightens the total time needed to complete the amplification.

In some previous automated PCR instruments, sample tubes are inserted into sample wells on a thermal block assembly. To perform the PCR process, the temperature of the thermal block assembly is cycled according to prescribed temperatures and times specified by the user in a PCR protocol file. The cycling is controlled by a computing system and associated electronics. As the thermal block assembly changes temperature, the samples in the various tubes experience similar changes in temperature. However, in these previous instruments differences in sample temperature are generated by thermal non-uniformity (TNU) from place to place within the thermal block assembly. Temperature gradients exist within the material of the block, causing some samples to have different temperatures than others at particular times in the cycle. Because the chemical reaction of the mixture has an optimum temperature for each or its stages, achieving that actual temperature is critical for good analytical results. A large TNU can cause the yield of the PCR process to differ from sample vial to sample vial.

As such, the analysis of TNU is an important attribute for characterizing the performance of a thermal block assembly, which may be used in various bioanalysis instrumentation. The TNU is typically measured in a sample block portion of a thermal block assembly, and is typically expressed as either the difference or the average difference between the hottest well and the coolest position on the sample block portion engaging a sample or samples. The industry standard, set in comparison with gel data, a difference of about 1.0° C., or an average difference of 0.5° C. Historically, the focus on reducing TNU has been focused on the sample block. For example, it has been observed that the edges of the sample block are typically cooler than the center. One approach that has been taken to counteract such edge effects is to provide various perimeter and edge heaters around the sample block to offset the observed thermal gradient from the center to the edges.

SUMMARY

In an exemplary embodiment, a method includes measuring a first temperature, by a first sensor, of a first sample block sector of a sample block using a thermoelectric controller, and measuring a second temperature, by a second sensor, of a second sample block sector of the sample block that is adjacent to the first sample block sector using the thermoelectric controller. The method further includes calculating, by a thermoelectric controller, a difference in temperature between the first temperature and the second temperature. The thermoelectric controller adjusts the first temperature of the first sample block sector based on the difference in temperature by adjusting a power output to one or more thermoelectric coolers. The thermoelectric coolers are configured to heat or cool the first sample block sector.

In another exemplary embodiment, a computer-readable storage medium is encoded with instructions for measuring a first temperature of a first sample block sector of a sample block using a thermoelectric controller, and measuring a second temperature of a second sample block sector of the sample block that is adjacent to the first sample block sector using the thermoelectric controller. The instructions are further for calculating a difference in temperature between the first temperature and the second temperature. The instructions further included instructions for adjusting the power output of the thermoelectric controller to one or more thermoelectric coolers to adjust the first temperature of the first sample block sector based on the difference in temperature. The thermoelectric coolers are configured to heat or cool the first sample block sector.

In another exemplary embodiment, a system includes a first sensor configured for detecting a first temperature of a first sample block sector of a sample block, and a second sensor configured for detecting a second temperature of a second sample block sector of the sample block that is adjacent to the first sample block sector. The system further includes a thermoelectric controller in electrical communication with the first sensor and the second sensor. The thermoelectric controller is configured to receive a first temperature of a first sample block sector of a sample block and receive a second temperature of a second sample block sector of the sample block that is adjacent to the first sample block sector. The thermoelectric controller if further configured to calculate a difference in temperature between the first temperature and the second temperature, and to adjust the first temperature of the first sample block sector based on the difference in temperature based on adjusting a power output to one or more thermoelectric coolers. The one or more thermoelectric coolers is configured to heat or cool the first sample block sector.

BRIEF DESCRIPTION OF THE DRAWINGS

The skilled artisan will understand that the drawings, described below, are for illustration purposes only. The drawings are not intended to limit the scope of the present teachings in any way.

DESCRIPTION OF VARIOUS EMBODIMENTS

In the following description, reference is made to the accompanying drawings that form a part thereof, and in which are shown by way of illustration specific exemplary embodiments in which the invention may be practiced. These embodiments are described in sufficient detail to enable those skilled in the art to practice the invention and it is to be understood that other embodiments may be utilized and that changes may be made within departing from the scope of the invention. The following description is, therefore, not to be taken in a limited sense.

Notwithstanding that the numerical ranges and parameters setting forth the broad scope of the invention are approximations, the numeral values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include an and all sub-ranges between (and including) the minimum value of zero and the maximum value of 10, that is, any and all sub-ranges having a minimum value of equal to or greater than zero and a maximum value of equal to or less than 10, e.g. 1 to 5.

In the present teachings, various embodiments of a thermal block assembly may have a plurality of thermal electric coolers (TECs), which may be controlled by a respective thermoelectric controller. According to various embodiments, control may be provided by a master controller or by the thermoelectric controllers. These controllers may provide dynamic adjustment of the TECs to achieve a desirable TNU of less than 0.5° C., for example.

As used herein, the terms "sample plate," "microtitration plate," "microtiter plate," and "microplate" are interchangeable and refer to a multi-welled sample receptacle for testing of chemical and biological samples. Microplates can have wells that are conical, cylindrical, rectilinear, tapered, and/or flat-bottomed in shape, and can be constructed of a single material or multiple materials. The microplate can conform to SBS Standard or it can be non-standard. Microplates can be open-face (e.g. closed with a sealing film or caps) or close-chambered (e.g. microcard as described in U.S. Pat. No. 6,825,047). Open-faced microplates can be filled, for example, with pipettes (hand-held, robotic, etc.) or throughhole distribution plates. Close-chambered microplates can be filled, for example, through channels or by closing to form the chamber.

Figure 1:
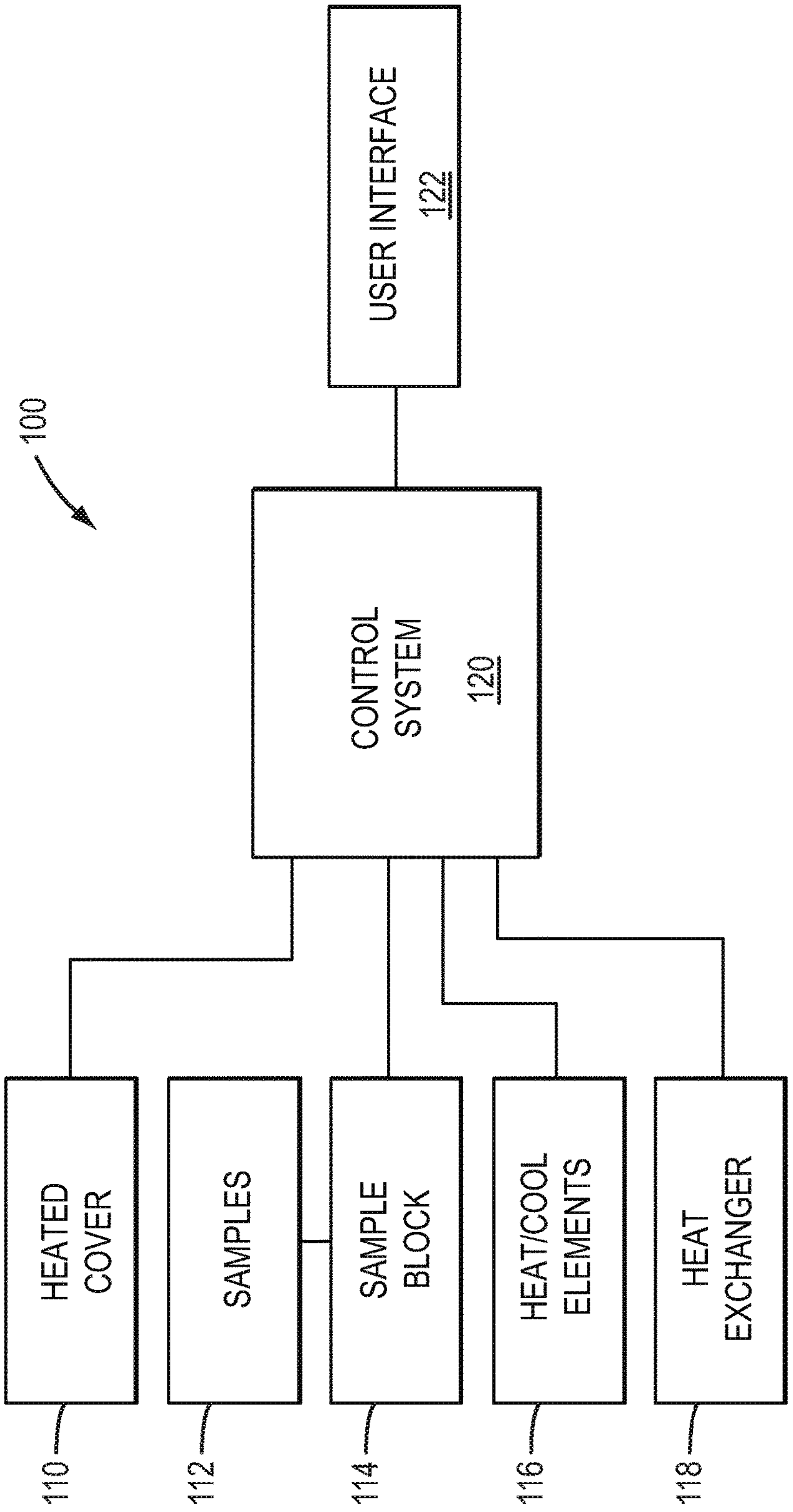
FIG. 1 is a block diagram of a thermal cycler instrument.
Figure 2:
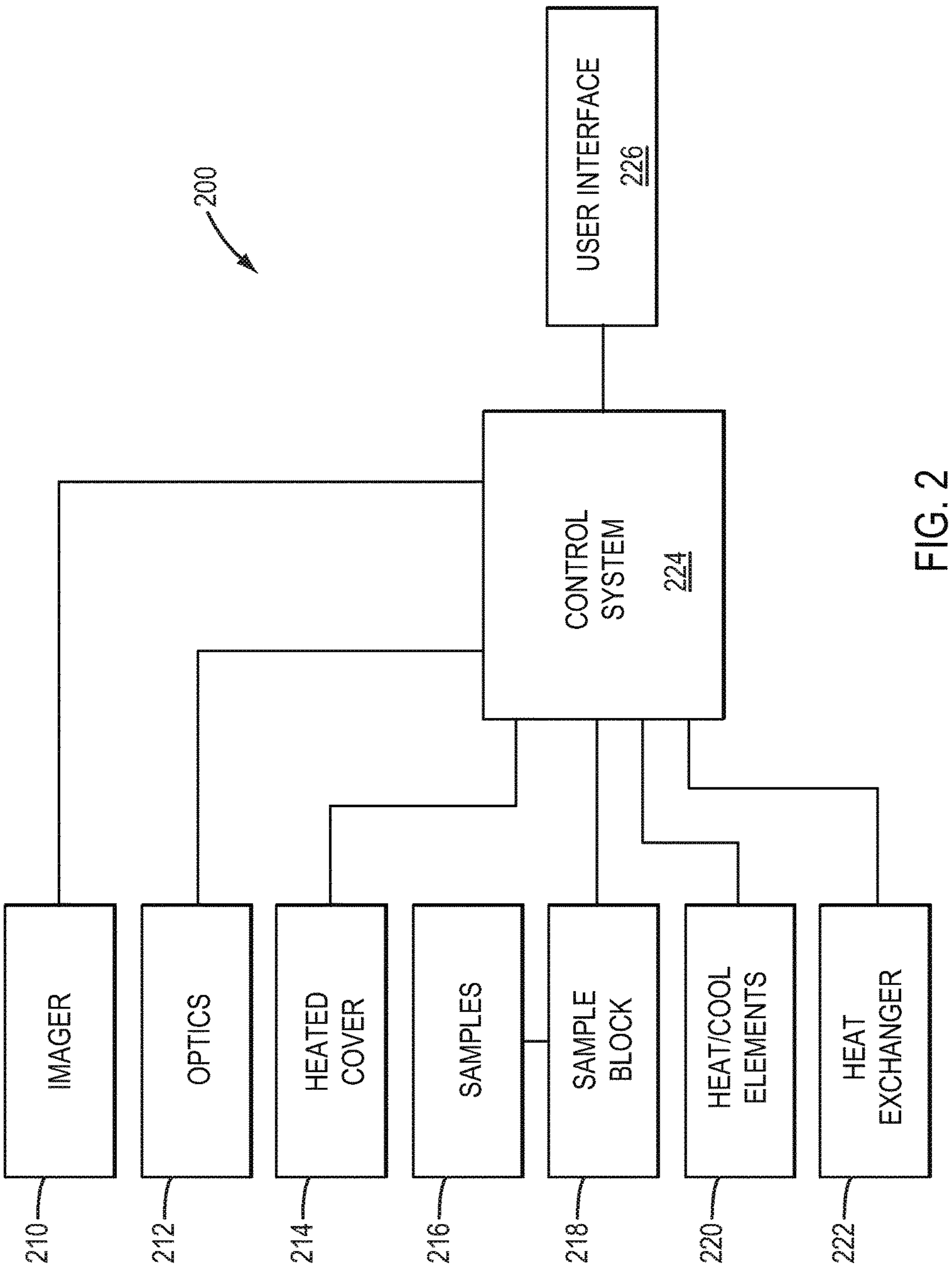
FIG. 2 is a block diagram of a thermal cycler instrument including a detection system.

Various embodiments of a thermal block assembly having uniform thermal distribution according to the present teachings may be used in various embodiments of a thermal cycler instrument as depicted in the block diagrams shown in FIG. 1 and FIG. 2.

According to various embodiments of a thermal cycler instrument 100, as shown in FIG. 1, a thermal cycling instrument may include a heated cover 110 that is placed over a plurality of samples 112 contained in a sample support device. In various embodiments, a sample support device may be a glass or plastic slide with a plurality of sample regions, which sample regions have a cover between the sample regions and heated lid 112. Some examples of a sample support device may include, but are not limited by, a multi-well plate, such as a standard microtiter 96-well, a 384-well plate, or a microcard, or a substantially planar support, such as a glass or plastic slide. The sample regions in various embodiments of a sample support device may include depressions, indentations, ridges, and combinations thereof, patterned in regular or irregular arrays formed on the surface of the substrate. Various embodiments of a thermal cycler instrument include a sample block 114, elements for heating and cooling 116, and a heat exchanger 118. Various embodiments of a thermal block assembly according to the present teachings comprise components 114-118 of thermal cycler system 100 of FIG. 1.

Figure 3:
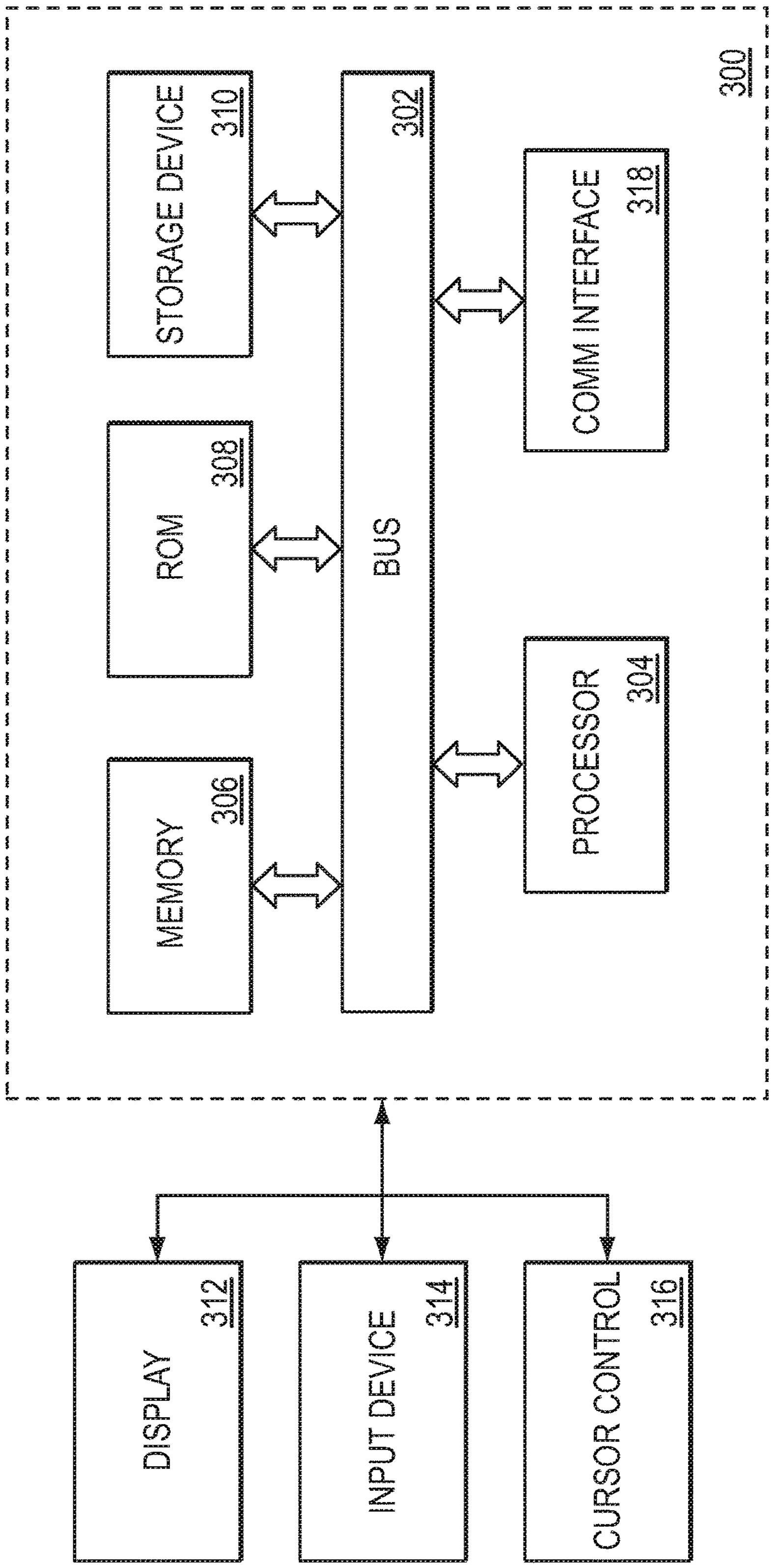
FIG. 3 is a block diagram that illustrates a computer system 700, according to various embodiments, upon which embodiments of methods for the analysis of PBA data may be implemented.

In FIG. 2, various embodiments of a thermal cycling system 200 have the components of embodiments of thermal cycling instrument 100, and additionally a detection system. A detection system may have an illumination source that emits electromagnetic energy, and a detector or imager 210. The detector or imager 210 is for receiving electromagnetic energy from samples 216 in sample support device. For embodiments of thermal cycler instrumentation 100 and 200, a control system 130 and 224, respectively, may be used to control the functions of the detection system, heated cover, and thermal block assembly, among other things. Control system 130 and 224 may be accessible to an end user through user interface 122 of thermal cycler instrument 100 and user interface 226 of thermal cycler instrument 200. A computing system 300, as depicted in FIG. 3 may provide the control the function of a thermal cycler instrument, as well as the user interface function. Additionally, computing system 300 may provide data processing, display and report preparation functions. All such instrument control functions may be dedicated locally to the thermal cycler instrument, or computing system 300 may provide remote control of part or all of the control, analysis, and reporting functions, as will be discussed in more detail subsequently.

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on computer-readable media. Some other processes can be implemented using analog circuitry, as is well known to one of ordinary skill in the art. Additionally, memory or other storage, as well as communication components, may be employed in embodiments of the invention.

FIG. 3 is a block diagram that illustrates a computer system 300 that may be employed to carry out processing functionality, according to various embodiments, upon which embodiments of a thermal cycler system 100 of FIG. 1 or a thermal cycler system 200 of FIG. 2 may utilize. Computing system 300 can include one or more processors, such as a processor 304. Processor 304 can be implemented using a general or special purpose processing engine such as, for example, a microprocessor, controller or other control logic. In this example, processor 304 is connected to a bus 302 or other communication medium.

Further, it should be appreciated that a computing system 300 of FIG. 3 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 300 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art.

Computing system 300 may include bus 302 or other communication mechanism for communicating information, and processor 304 coupled with bus 302 for processing information.

Computing system 300 also includes a memory 306, which can be a random access memory (RAM) or other dynamic memory, coupled to bus 302 for storing instructions to be executed by processor 304. Memory 306 also may be used for storing temporary variables or other intermediate information during execution of instructions to be executed by processor 304. Computing system 300 further includes a read only memory (ROM) 308 or other static storage device coupled to bus 302 for storing static information and instructions for processor 304.

Computing system 300 may also include a storage device 310, such as a magnetic disk, optical disk, or solid state drive (SSD) is provided and coupled to bus 302 for storing information and instructions. Storage device 310 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 310 may include other similar instrumentalities for allowing computer programs or other instructions or data to be loaded into computing system 300. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 310 to computing system 300.

Computing system 300 can also include a communications interface 318. Communications interface 318 can be used to allow software and data to be transferred between computing system 300 and external devices. Examples of communications interface 318 can include a modem, a network interface (such as an Ethernet or other NIC card), a communications port (such as for example, a USB port, a RS-232C serial port), a PCMCIA slot and card, Bluetooth, etc. Software and data transferred via communications interface 318 are in the form of signals which can be electronic, electromagnetic, optical or other signals capable of being received by communications interface 318. These signals may be transmitted and received by communications interface 318 via a channel such as a wireless medium, wire or cable, fiber optics, or other communications medium. Some examples of a channel include a phone line, a cellular phone link, an RF link, a network interface, a local or wide area network, and other communications channels.

Computing system 300 may be coupled via bus 302 to a display 312, such as a cathode ray tube (CRT) or liquid crystal display (LCD), for displaying information to a computer user. An input device 314, including alphanumeric and other keys, is coupled to bus 302 for communicating information and command selections to processor 304, for example. An input device may also be a display, such as an LCD display, configured with touchscreen input capabilities. Another type of user input device is cursor control 316, such as a mouse, a trackball or cursor direction keys for communicating direction information and command selections to processor 304 and for controlling cursor movement on display 312. This input device typically has two degrees of freedom in two axes, a first axis (e.g., x) and a second axis (e.g., y), that allows the device to specify positions in a plane. A computing system 300 provides data processing and provides a level of confidence for such data. Consistent with certain implementations of embodiments of the present teachings, data processing and confidence values are provided by computing system 300 in response to processor 304 executing one or more sequences of one or more instructions contained in memory 306. Such instructions may be read into memory 306 from another computer-readable medium, such as storage device 310. Execution of the sequences of instructions contained in memory 306 causes processor 304 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 304 for execution. Such instructions, generally referred to as "computer program code" (which may be grouped in the form of computer programs or other groupings), when executed, enable the computing system 300 to perform features or functions of embodiments of the present invention. These and other forms of computer-readable media may take many forms, including but not limited to, non-volatile media, volatile media, and transmission media. Non-volatile media includes, for example, solid state, optical or magnetic disks, such as storage device 310. Volatile media includes dynamic memory, such as memory 306. Transmission media includes coaxial cables, copper wire, and fiber optics, including the wires that comprise bus 302.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 304 for execution. For example, the instructions may initially be carried on magnetic disk of a remote computer. The remote computer can load the instructions into its dynamic memory and send the instructions over a telephone line using a modem. A modem local to computing system 300 can receive the data on the telephone line and use an infra-red transmitter to convert the data to an infra-red signal. An infra-red detector coupled to bus 302 can receive the data carried in the infra-red signal and place the data on bus 302. Bus 302 carries the data to memory 306, from which processor 304 retrieves and executes the instructions. The instructions received by memory 306 may optionally be stored on storage device 310 either before or after execution by processor 304.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Sample Block

A thermal block assembly includes a sample block, one or more heating/cooling devices, and a heat exchanger, for example. The sample block receives a microtiter plate with several reaction vessels. The sample block may have several recesses configured in a regular pattern to receive the respective reaction vessels. The one or more heating/cooling devices in concert with the heat exchanger are designed to provide heating and cooling for the sample block. The one or more heating/cooling devices can include a thermoelectric cooler (TEC), e.g. a Peltier device, to provide both heating and cooling.

A heating device may be a resistive heater, known to one of ordinary skill in the art. This heating device may be shaped, for example, as coils or loops to distribute heat uniformly across a segment. Alternatively, the heating device can be a resistive ink heater, or an adhesive backed heater, such as a Kapton heater.

Figure 4:
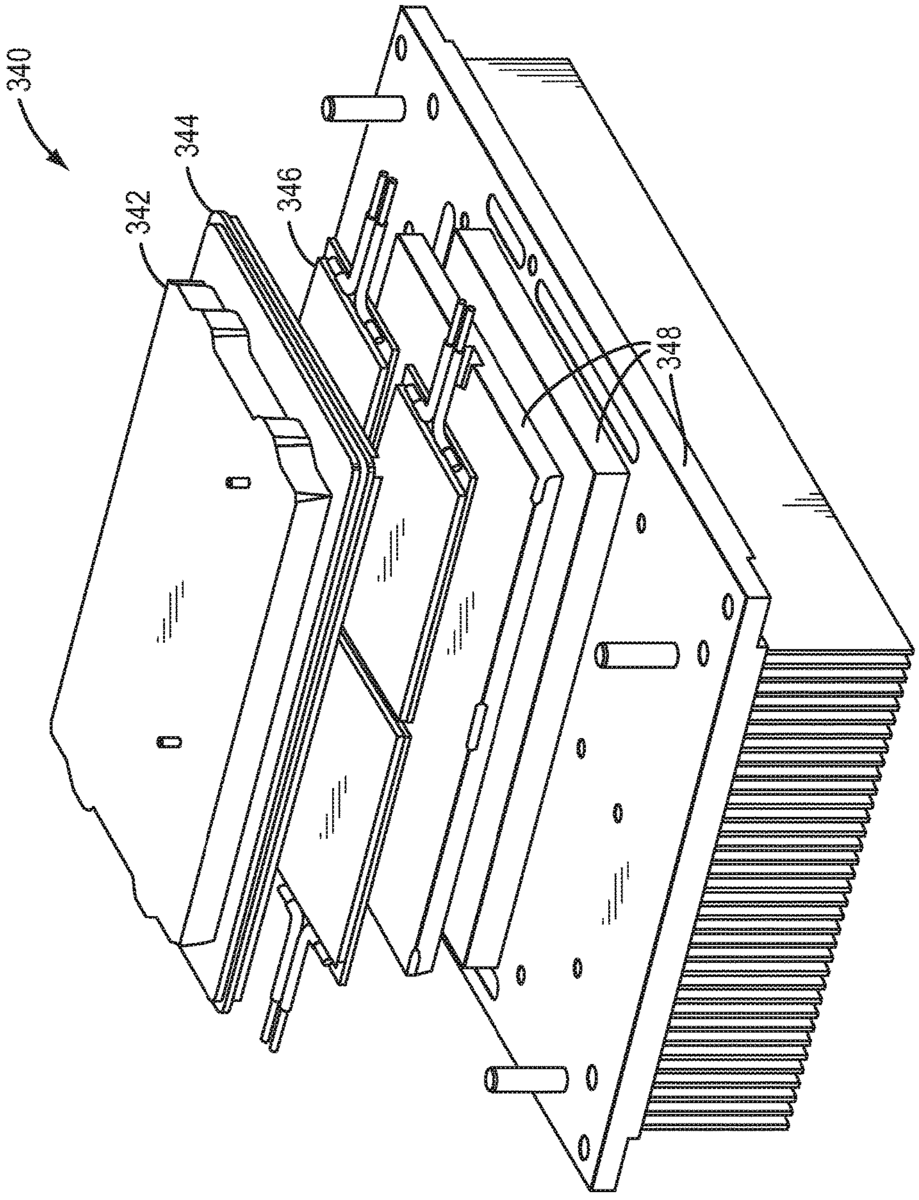
FIG. 4 illustrates a perspective of an exemplary thermal block assembly.

A sample block is logically or physically divided into several sample block sectors (SS). Each SS is assigned a heating device and a cooling device or a heating and cooling device that may actuate each SS independently. FIG. 4 illustrates a perspective view of an exemplary thermal block assembly 340. Thermal block assembly 340 includes reaction vessel 342, sample block 344, TEC 346, and heat exchanger 348. As shown in FIG. 4, different sample block sectors of a sample block may be heated and cooled by a matrix, e.g. 2×2, of heating and cooling elements of TEC 346.

Figure 5:
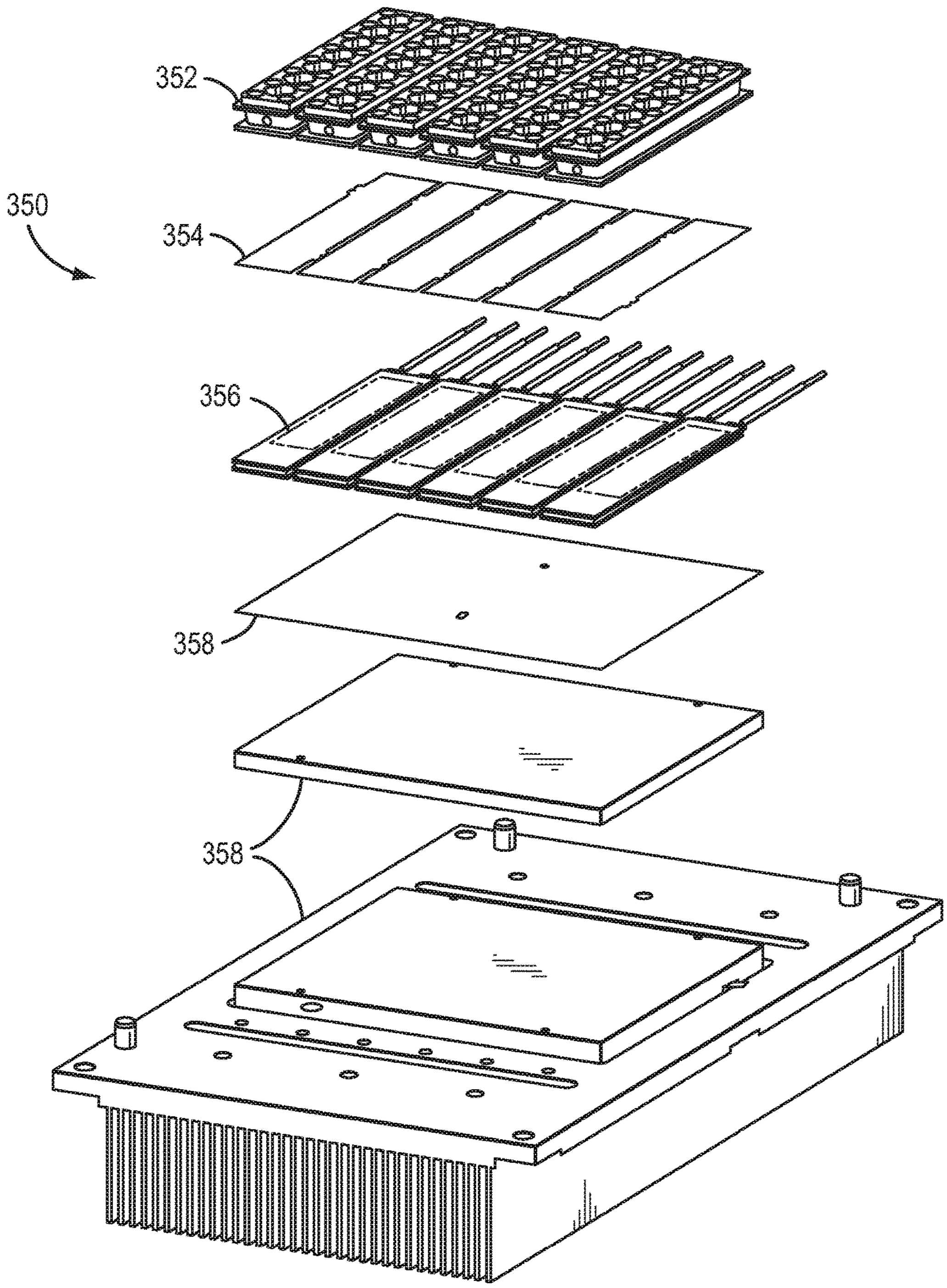
FIG. 5 illustrates a generalized schematic that depicts a prior art control system for the thermal block assembly shown in FIG. 4.

FIG. 5 illustrates a perspective view of another exemplary thermal block assembly 350. Thermal block assembly 350 includes reaction vessel 352, sample block 354, TEC 356, and heat exchanger 358. As shown in FIG. 5, a sample block may also be heated and cooled using a linear array of heating and cooling elements of TEC 356.

Sample Block Control System

Figure 6:
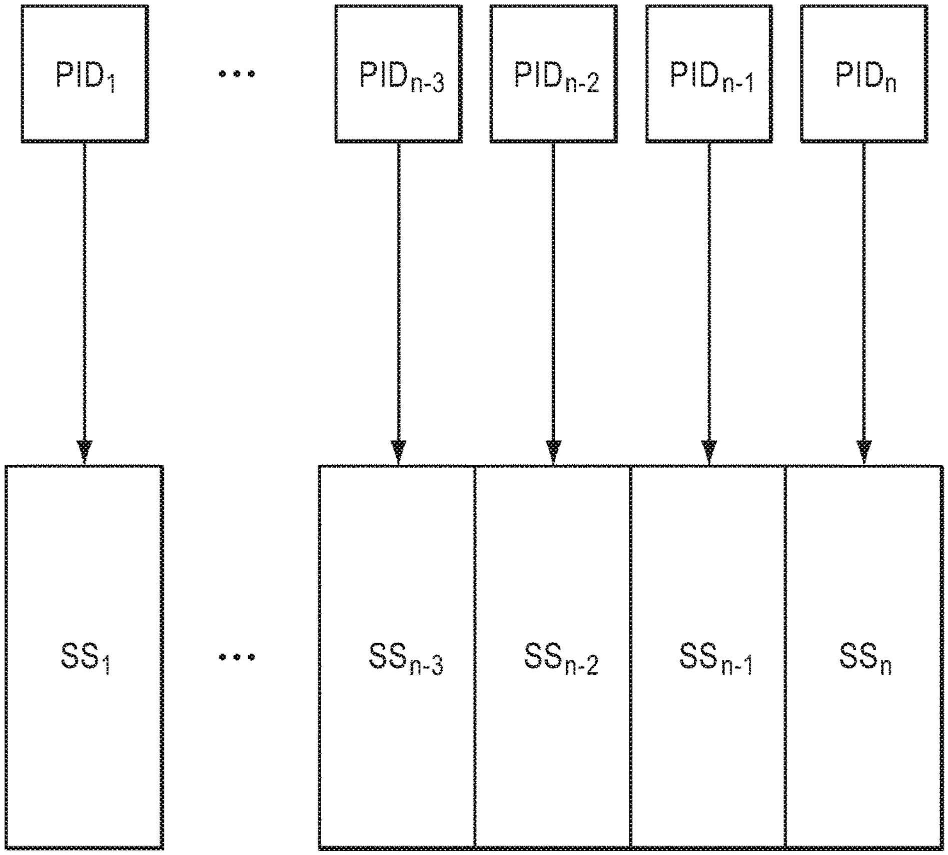
FIG. 6 (PRIOR ART)
FIG. 6 illustrates a generalized schematic for a prior art control system for the thermal block assembly shown in FIG. 5.

FIG. 6 illustrates a generalized schematic for a control system for the thermal block assembly shown in FIG. 5. Each proportional integrated derivative (PID) controller controls a separate sample block sector (SS).

Generally, in some previous automated PCR instruments, the temperature of the metal sample block is cycled according to prescribed temperatures and times specified by the user in a PCR protocol file. The cycling is controlled by a computing system and associated electronics. As the metal block changes temperature, the samples in the various tubes experience similar changes in temperature. However, in these instruments, differences in sample temperature are generated by non-uniformity of temperature from place to place within the sample metal block. Temperature gradients exist within the material of the block, causing some samples to have different temperatures than others at particular times in the cycle. Further, there are delays in transferring heat from the sample block to the sample, and those delays differ across the sample block. The differences in temperature and delays in heat transfer cause the yield of the PCR process to differ from sample vial to sample vial. To perform the PCR process more uniformly and efficiently and to enable so-called quantitative PCR, these time delays and temperature errors should be minimized. The problems of minimizing non-uniformity in temperature at various points on the sample block and the time required for heat transfer to and from the sample become particularly acute when the size of the region containing samples becomes large as in standard 8 by 12 microtiter plate.

Another problem with automated PCR instruments is accurately predicting the actual temperature of the reaction mixture during temperature cycling. Because the chemical reaction or the mixture has an optimum temperature for each of its stages, achieving that actual temperature is important for good analytical results. Actual measurement of the temperature of the mixture in each vial is impractical because of the small volume of each vial and the large number of vials.

FIGS. 7-23 depict exemplary embodiments of methods and systems of uniform control of the temperature using a control system such as PID controllers or a master system controller. Disclosed herein are embodiments of an instrument including a thermal sample block assembly configured for improved thermal uniformity for PCR by dynamically adjusting sample block sector temperatures. The thermal block assembly includes a plurality of thermal electric coolers (TECs), controlled for thermal cycling. In various embodiments, the TECs are controlled by a respective thermoelectric controller. System feedback control receives environmental parameters from at least two thermoelectric controllers. System feedback control is provided by a master controller or within the thermoelectric controllers. Examples of environmental parameters include local sample block temperature, ambient temperature, and local sample temperature. Based on the received data, local sample block temperature set points are recalculated and transmitted to the local thermoelectric controllers.

Figure 7:
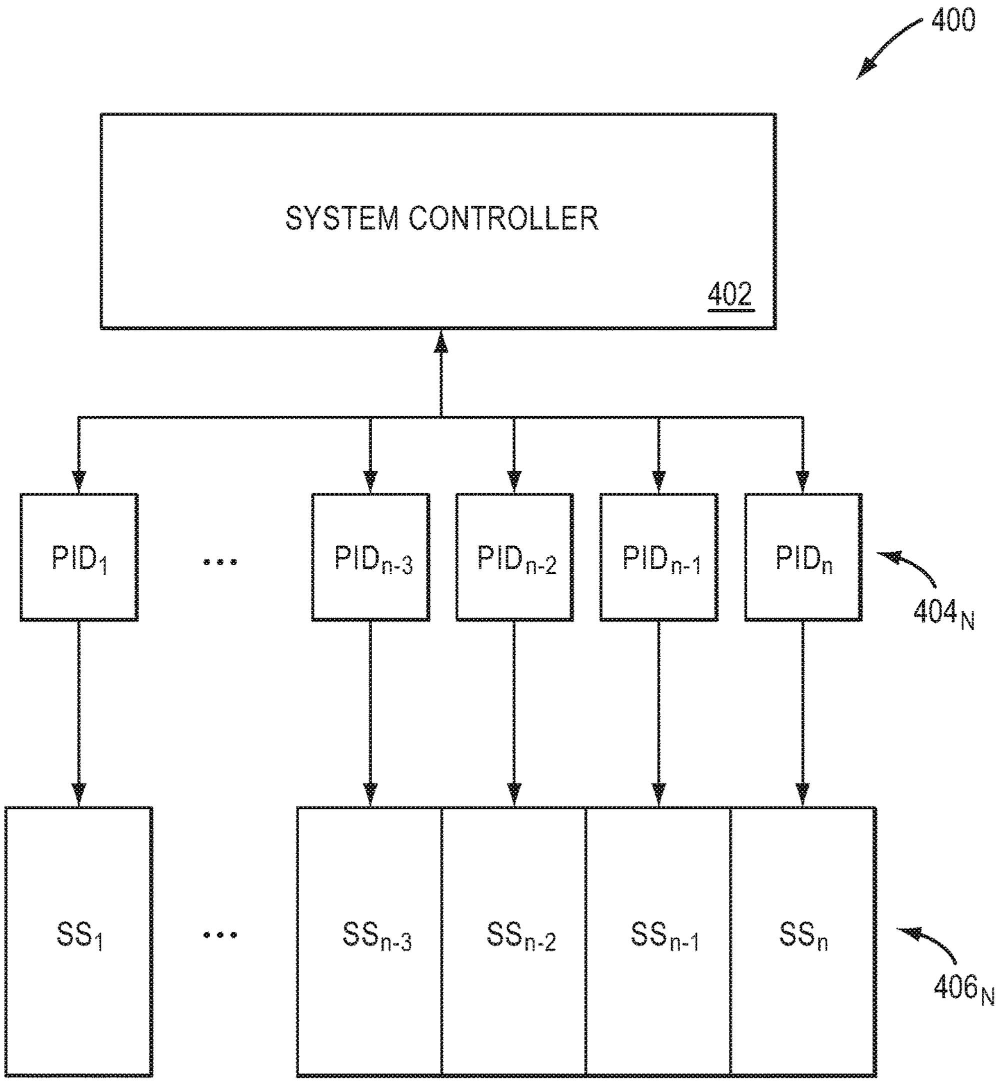
FIG. 7 illustrates a schematic representation 400 corresponding to an embodiment.

FIG. 7 illustrates a schematic representation 400 corresponding to an embodiment. System controller 402 is a master system controller that is bidirectionally connected to each thermoelectric controller, e.g. proportional integrated derivative (PID) controllers $\mathbf{404}_N$. Each PID controller $\mathbf{404}_N$ is connected to a respective sample block sector (SS) $\mathbf{406}_N$. System controller 402 controls the temperature of the sample block according to at least one environmental parameter received from each of the thermoelectric controllers. System controller 402 determines new thermal set points from the environmental parameters to maintain a uniform temperature.

The environmental parameters may include temperature parameters such as sample block temperature, ambient temperature, and local sample temperature. System controller 402 receives the environmental parameters periodically, aperiodically, or upon querying the thermoelectric controllers.

While the sample block sectors are depicted in a linear array, the sample block sectors may be configured in a matrix array, e.g. m× n, where m≥1 and n≥2. The sample block may be formed of any material that exhibits good thermal conductivity including, but not limited to, metals, such as aluminum, silver, gold, and copper, carbon or other conductive polymers. The sample block may be configured to receive one microtiter plate. For example, the top of the sample block can include a plurality of recessed wells arranged in an array that corresponds to the wells in the microtiter plate. For example, common microtiter plates can include 96 depressions arranged as an 8×12 array, 384 depressions arranged as a 16×24 array, and 48 depressions arranged as a 8×6 array or 16×3 array.

Each sample block sector further includes a thermoelectric (TEC) device, such as, for example, a Peltier device. The plurality of TECs can be configured to correspond to the plurality of zones. The TEC can provide all heating and cooling. As used herein, the term “control temperature” refers to any desired temperature that can be set by a user, such as, for example, temperatures for denaturing, annealing, and elongation during PCR reactions. Each of the plurality of TECs can function independently without affecting other of the plurality of TECs. In conjunction with the system controller, this can provide improved thermal uniformity for the plurality of sample block sectors.

Figure 8:
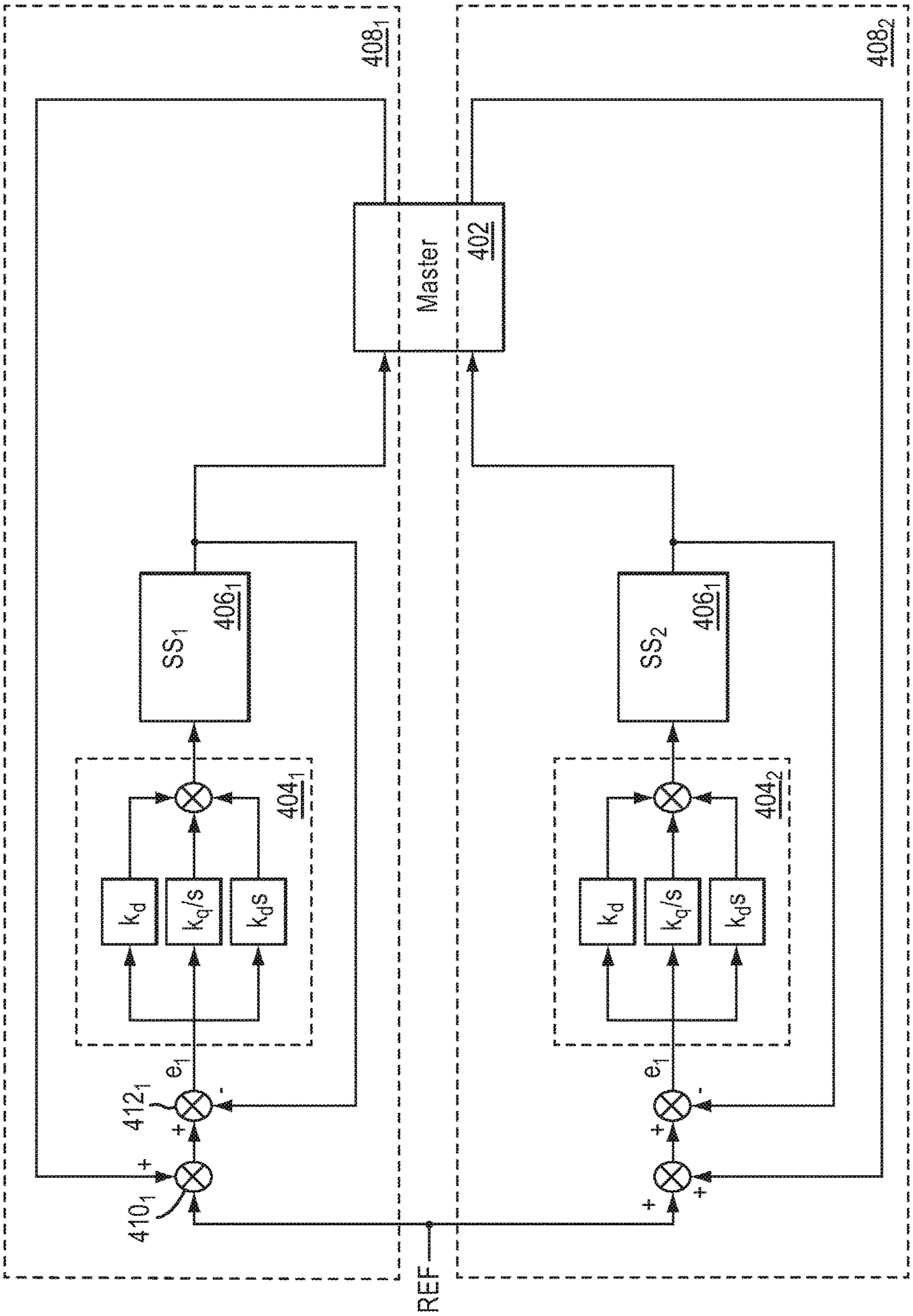
FIG. 8 illustrates a functional block diagram corresponding to an embodiment.

FIG. 8 illustrates a functional block diagram corresponding to an embodiment. This embodiment shows the master system controller 402 bidirectionally communicating with two thermoelectric controllers, e.g. PID controllers $\mathbf{404}_1$, $\mathbf{404}_2$.

For each PID leg $\mathbf{408}_N$, the first mixer $\mathbf{410}_N$ receives the reference signal and block sensor temperature difference (BSTD) process variable. The second mixer $\mathbf{412}_N$ receives the output signal of the first mixer $\mathbf{410}_N$ and the output of the sample block sector $\mathbf{406}_N$. The output of the sample block sector $\mathbf{406}_N$ corresponds to the measurement of the desired environmental parameter. The output of the second mixer $\mathbf{412}_N$ is applied to the thermoelectric controller, e.g. PID controller $\mathbf{406}_N$. The output of the PID controller $\mathbf{404}_N$ is applied to the sample block sector $\mathbf{406}_N$.

The master system controller 402 receives the environmental parameter data from each of the sample block sectors $\mathbf{406}_1$, $\mathbf{406}_2$. The master system controller 402 determines a BSTD variable appropriate for each PID leg $\mathbf{408}_1$, $\mathbf{408}_2$. The master system controller 402 may be implemented by a microprocessor, for example.

Figure 9:
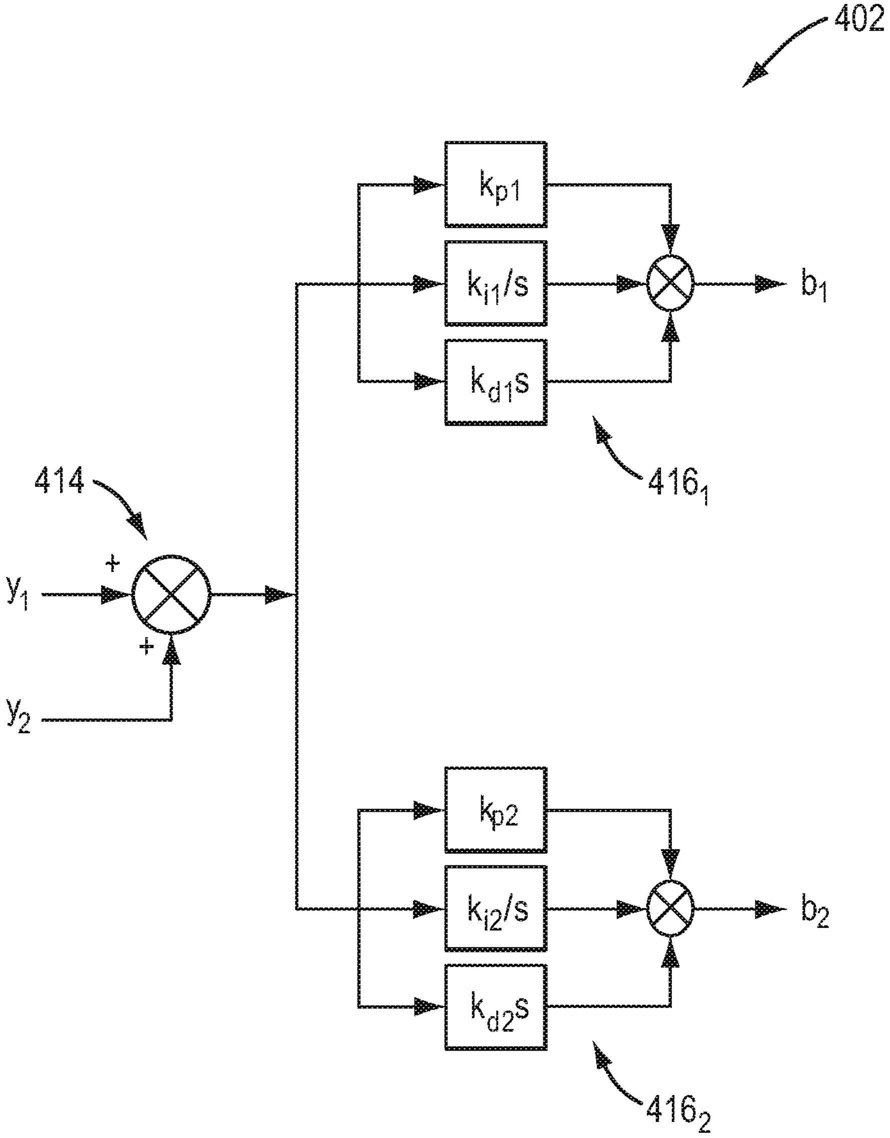
FIG. 9 illustrates a functional block diagram corresponding to an embodiment.

FIG. 9 illustrates a schematic representation of the master system controller 402 shown in FIG. 8. A mixer 414 receives inputs $y_1$ and $y_2$. The output of the mixer 414 is applied as input to two master PID controllers $\mathbf{416}_1$, $\mathbf{416}_2$. The first master PID controller $\mathbf{416}_1$ calculates the new set point $b_1$ for the first external PID controller $404_1$. The second master PID controller $416_2$ calculates the new set point $b_2$ for the second external PID controller $404_2$.

Figure 10:
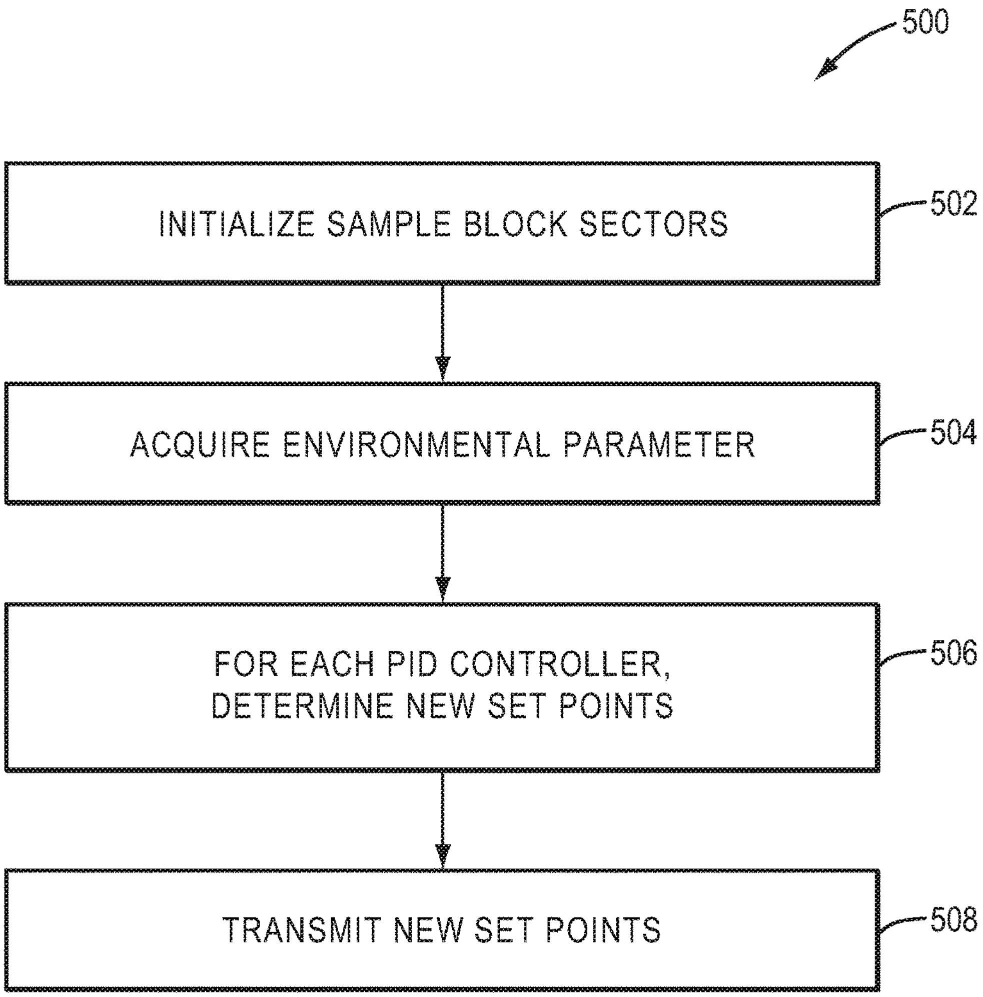
FIG. 10 illustrates a process flow chart 500 according to the embodiment shown in FIG. 9.

FIG. 10 illustrates a process flow chart 500 according to the embodiment shown in FIG. 9. In step 502, the temperature of the sample block sectors is initialized. In step 504, the master system controller acquires environmental parameters for each of the PID controllers. In step 506, the master system controller determines a new set point for each of the PID controllers. In step 508, the master system controller transmits new set points for each of the PID controllers.

Figure 11:
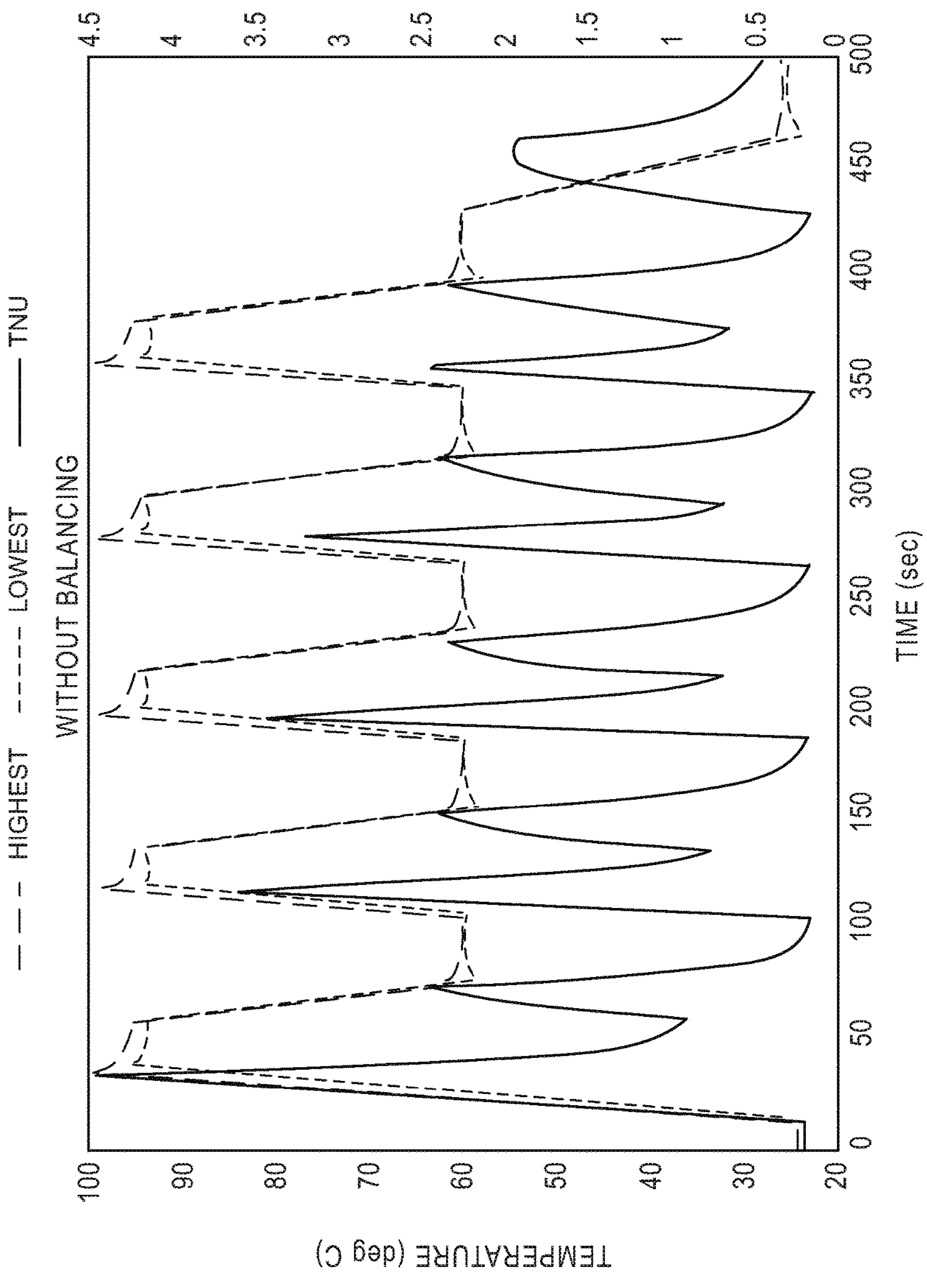
FIG. 11 is a graph illustrating a two PID controller system without a master system controller.
Figure 12:
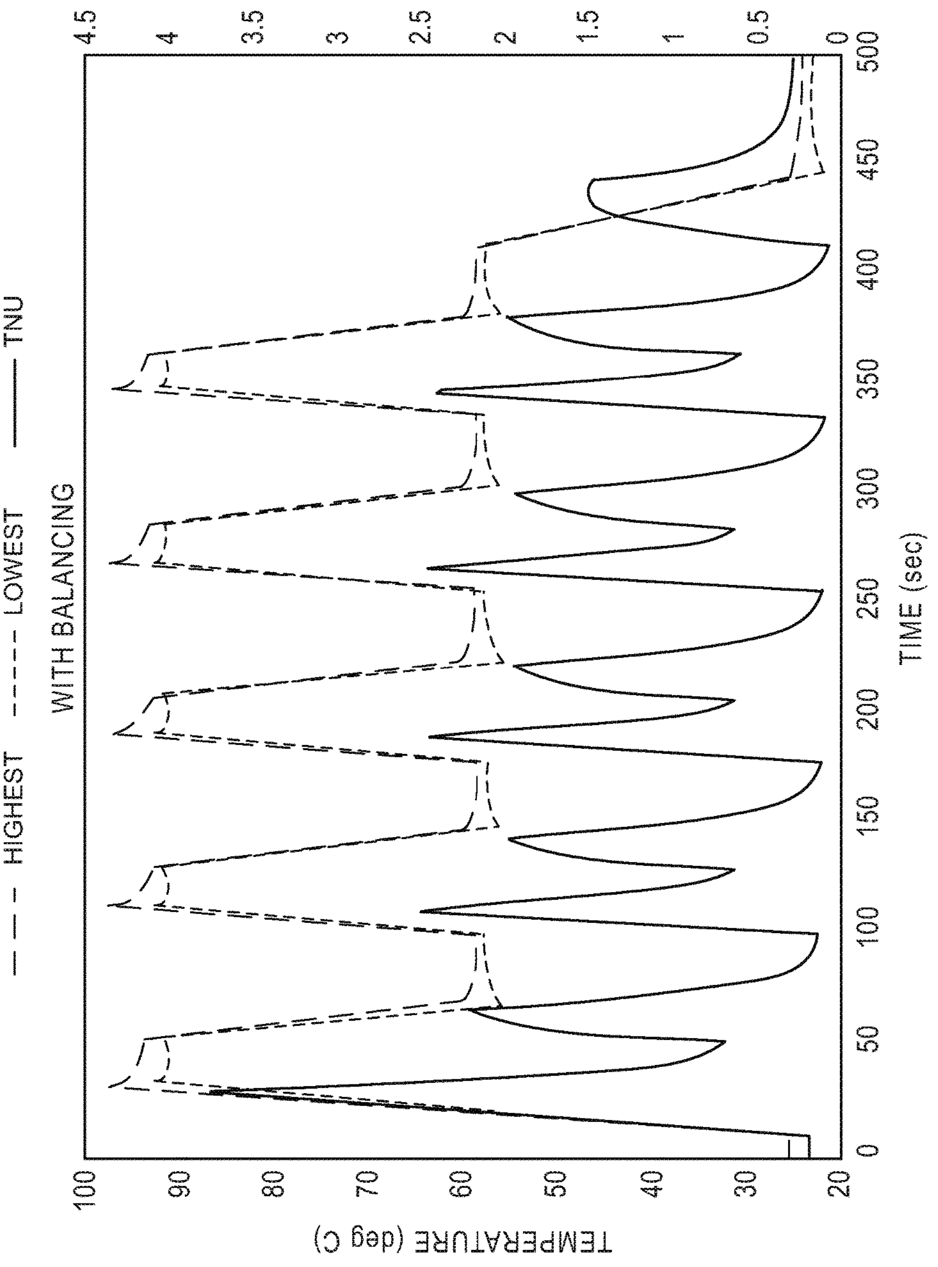
FIG. 12 is a graph illustrating a two PID controller system with a master system controller.

FIGS. 11 and 12 illustrate data collected before and after a master system controller is implemented. FIG. 11 is a graph illustrating a two PID controller system without a master system controller. FIG. 12 is a graph illustrating a two PID controller system with a master system controller.

Figure 13:
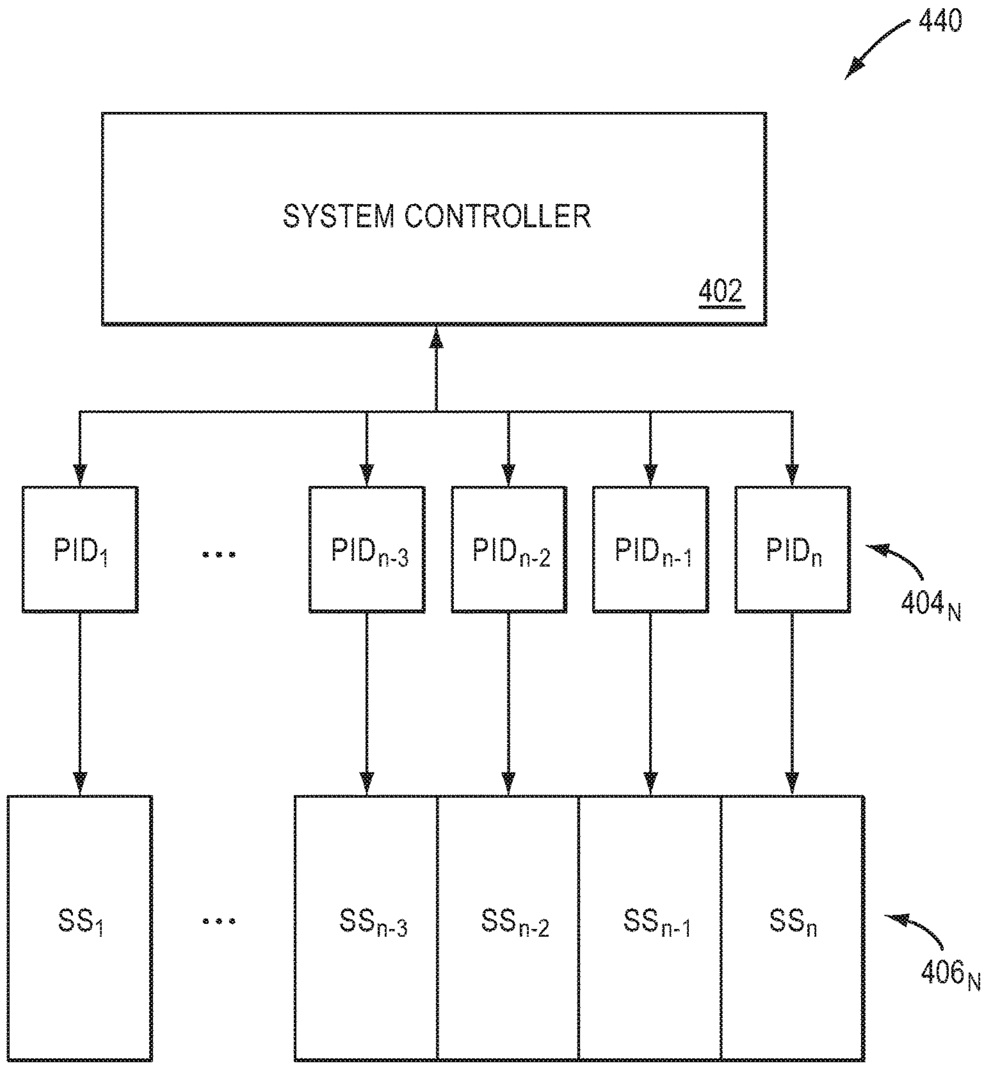
FIG. 13 illustrates a schematic representation 410 corresponding to an embodiment.

FIG. 13 illustrates a schematic representation 440 corresponding to an embodiment. System controller is a master system controller 402 that is bidirectionally connected to the external PID controllers $404_1$, $404_n$. Each PID controller $404_N$ is connected to a respective sample block sector $406_N$.

Figure 14:
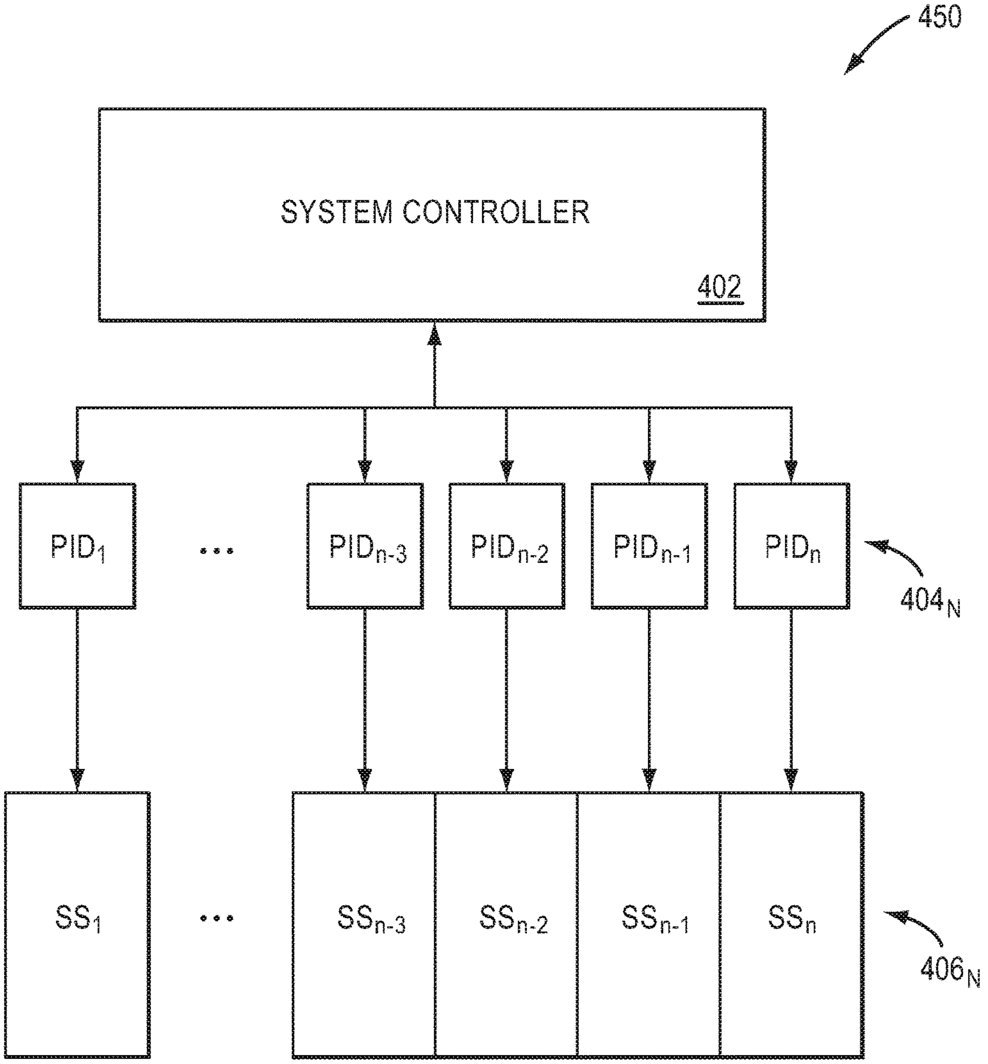
FIG. 14 illustrates a schematic representation 420 corresponding to an embodiment.

FIG. 14 illustrates a schematic representation 450 corresponding to an embodiment. System controller is a master system controller 402 that is bidirectionally connected to the external PID controllers $404_1$, $404_n$ and at least one internal PID controller $404_{n-2}$. Each PID controller $404_N$ is connected to a respective sample block sector $406_N$.

Figure 15:
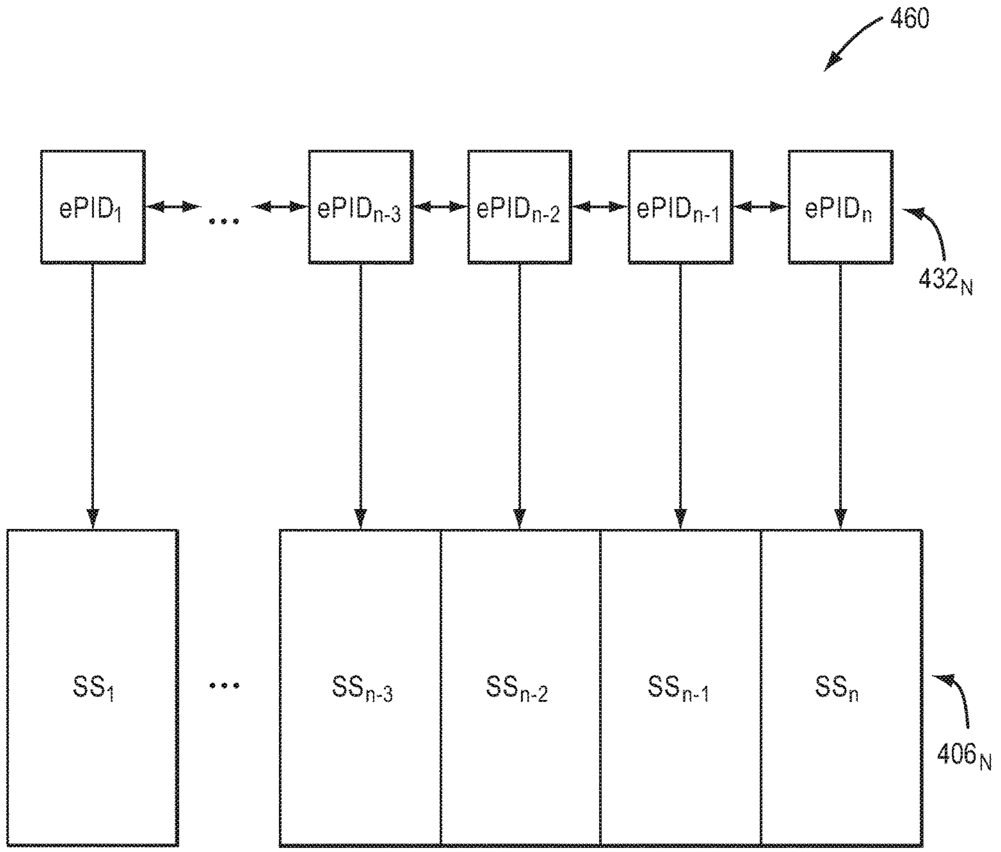
FIG. 15 illustrates a schematic representation 430 corresponding to an embodiment.

In one embodiment the functionality of the system controller is included within each of the PID controllers. FIG. 15 illustrates a schematic representation 460 corresponding to an embodiment. The functionality of the system controller is distributed between the each of the enhanced PID controllers $432_N$. Each enhanced PID controller $432_N$ is connected to a respective sample block sector $406_N$.

While the sample block sectors are depicted in a linear array, the sample block sectors may be placed in a matrix array, e.g. m× n, where m≥1 and n≥2. In an embodiment, adjacent sample block sectors may be controlled by a pair of PID control sections.

Figure 16:
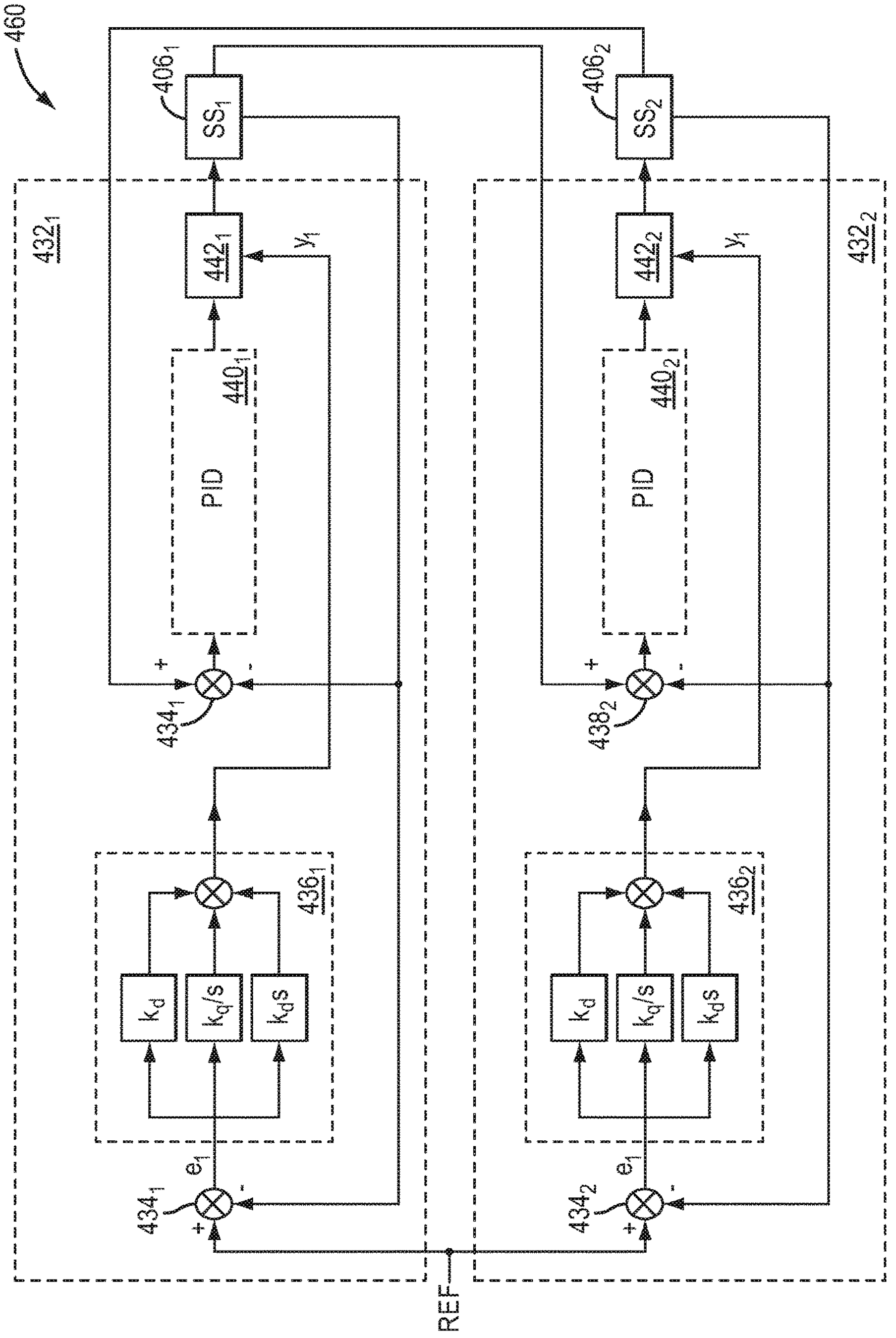
FIG. 16 illustrates a functional block diagram of the system controller according to a two plant embodiment for the embodiment shown in FIG. 14.

FIG. 16 illustrates a functional block diagram of system controller 460 according to a two PID controller embodiment for the embodiment shown in FIG. 15.

For each enhanced PID controller $432_N$, a first mixer $434_N$ receives the reference signal and BSTD process variable from the sample block sector $406_N$. A first PID controller $436_N$ receives the output signal from the first mixer $434_N$. A second mixer $438_N$ receives the environmental parameter data from each sample block sector $406_1$, $406_2$. A second PID controller $440_N$ receives the output from the second mixer $438_N$. An internal plant $442_N$ receives the output signals of the first and the second PID controllers $436_N$, $440_N$ to determine the correction to be applied to the respective sample block sector.

Figure 17:
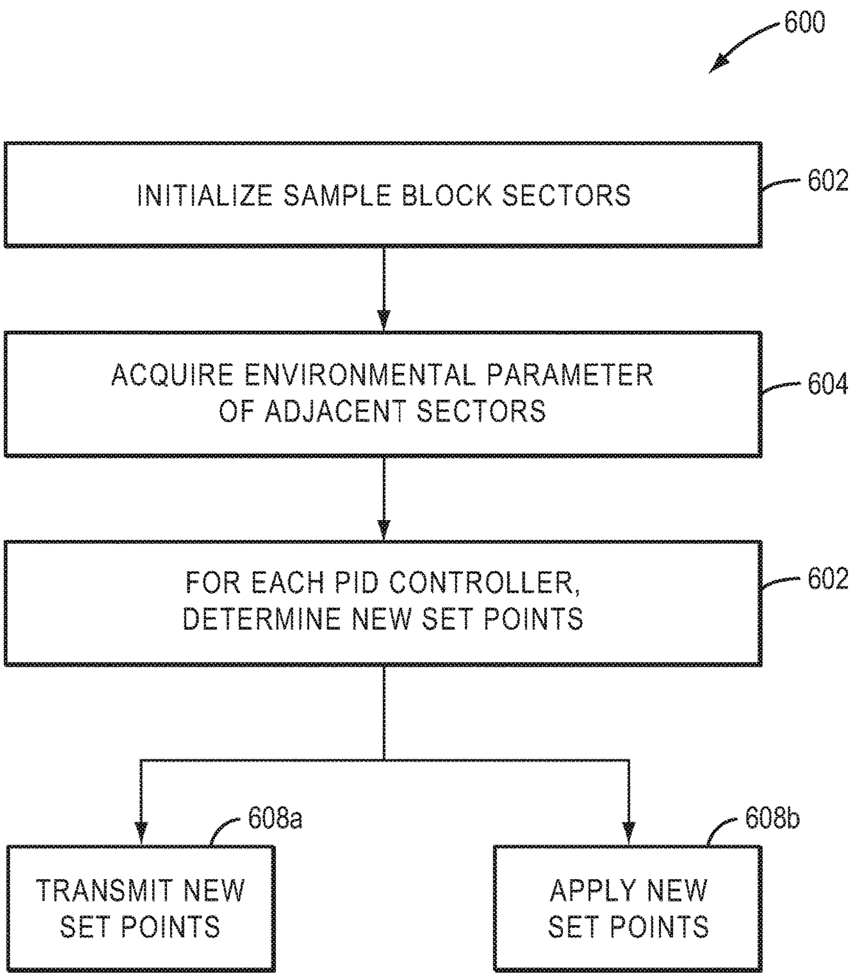
FIG. 17 illustrates a process flowchart 600 according to the embodiment shown in FIG. 15.

FIG. 17 illustrates a process flowchart 600 according to the embodiment shown in FIG. 15. In step 602, the sample block sectors are initialized. In step 604, the distributed system controller, e.g. each of the enhanced PID controllers, acquires environmental parameters of adjacent sample sectors. In step 606, the distributed system controller determines new set points. In step 608*a*, the new set points for an adjacent sample block sector may be transmitted. Alternatively, in step 608*b*, the new set points may be applied for the sample block sector of the respective portion of the distributed system controller.

Figure 18:
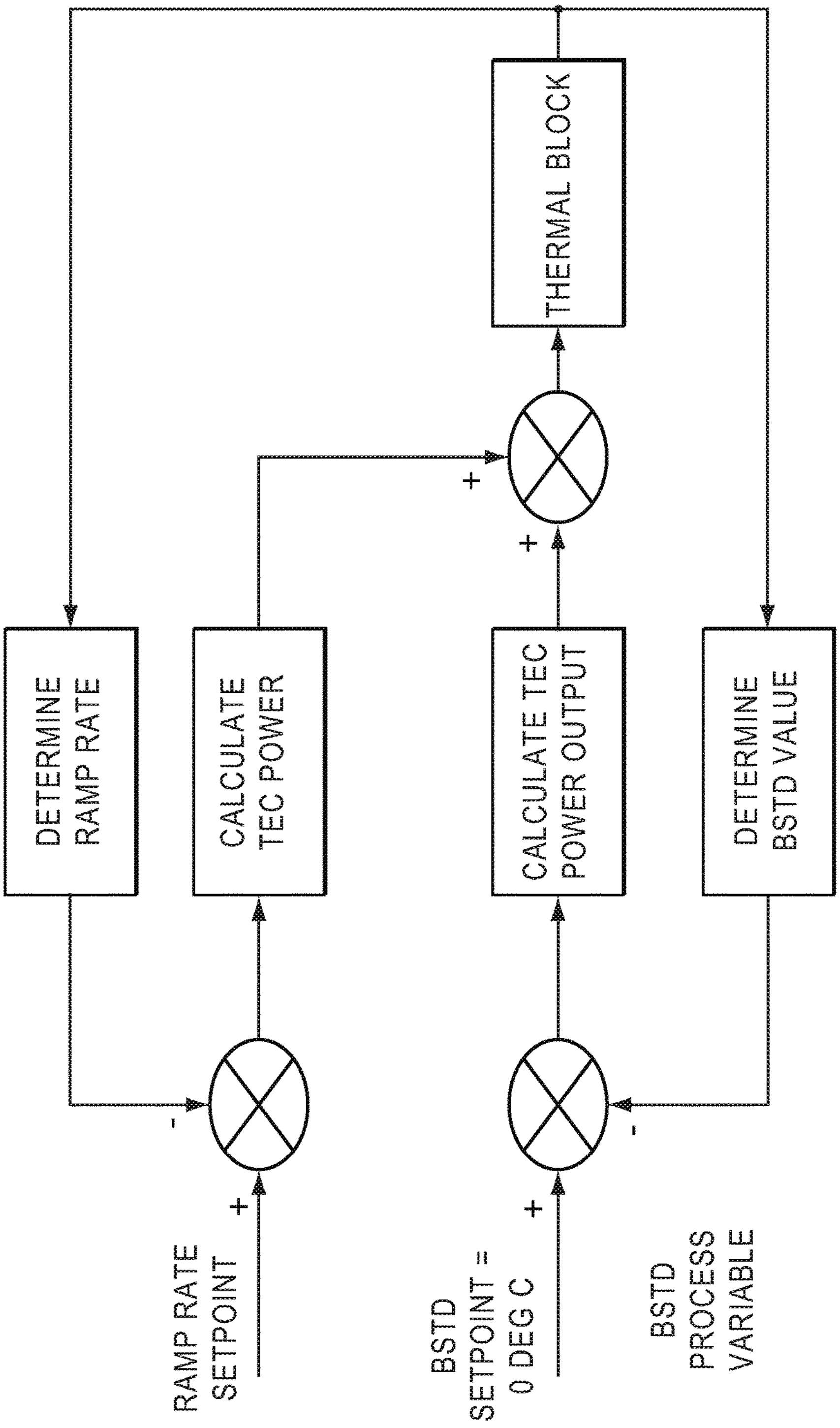
FIG. 18 illustrates a functional block diagram for each PID controller shown in FIG. 14.
Figure 19:
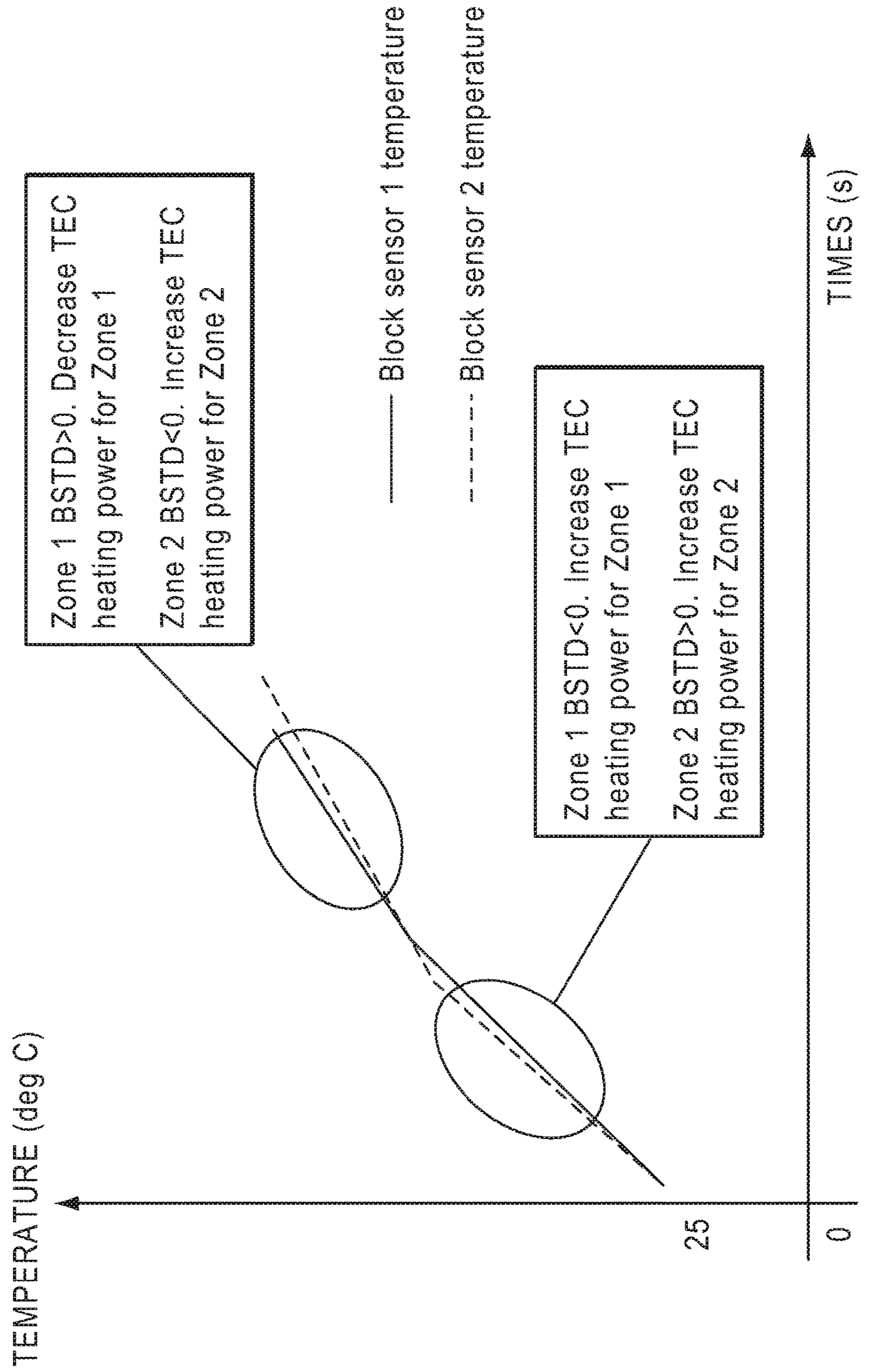
FIG. 19 is a graph illustrating a two PID controller system with a distributed system controller within the PID controllers.

FIG. 18 illustrates a functional block diagram showing each enhanced PID controller for the two PID controller embodiments shown in FIG. 15 and FIG. 16. FIG. 19 is a graph illustrating the control logic in a two PID controller system with a distributed system controller within the enhanced PID controllers.

In FIG. 18 a first mixer receives the block sensor temperature difference (BSTD) set point and a BSTD process variable. The first mixer output is used to determine a first power output to the TEC. The block temperature from each block sensor is used to determine the BSTD process variable. A second mixer receives the ramp rate set point and a determined ramp rate. The second mixer output is used to determine the power output to a second TEC. A third mixer receives the power output for the first TEC and the power output for the second TEC. The third mixer output is sent to the TECs of the sample block sector.

The BSTD value is controlled by employing a PID control algorithm, with corresponding parameters that can be tuned to adjust the power of the TEC output based on the feedback from the BSTD value. The target set for PID control is to have BSTD value of 0.

The PID control of BSTD is performed during the ramping up and ramping down state of the thermal block control. The power output to the TEC of each thermal zone is computed from the output from PID control of ramp rate control as well as the output from the PID control of BSTD. The output to the TEC is controlled to obtain BSTD set and ramp rate set accordingly.

Figure 20:
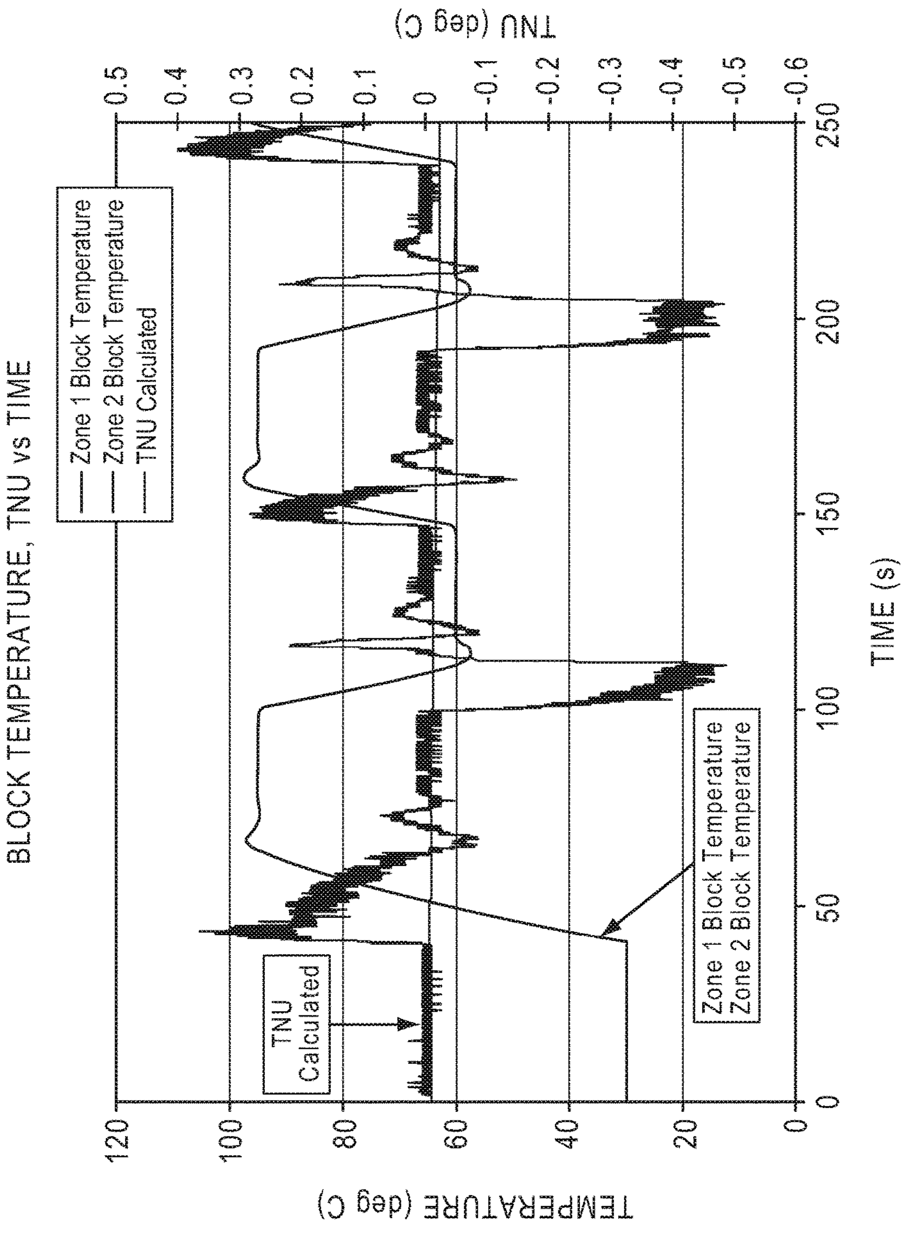
FIG. 20 is a graph illustrating a two PID controller system without a distributed system controller.
Figure 21:
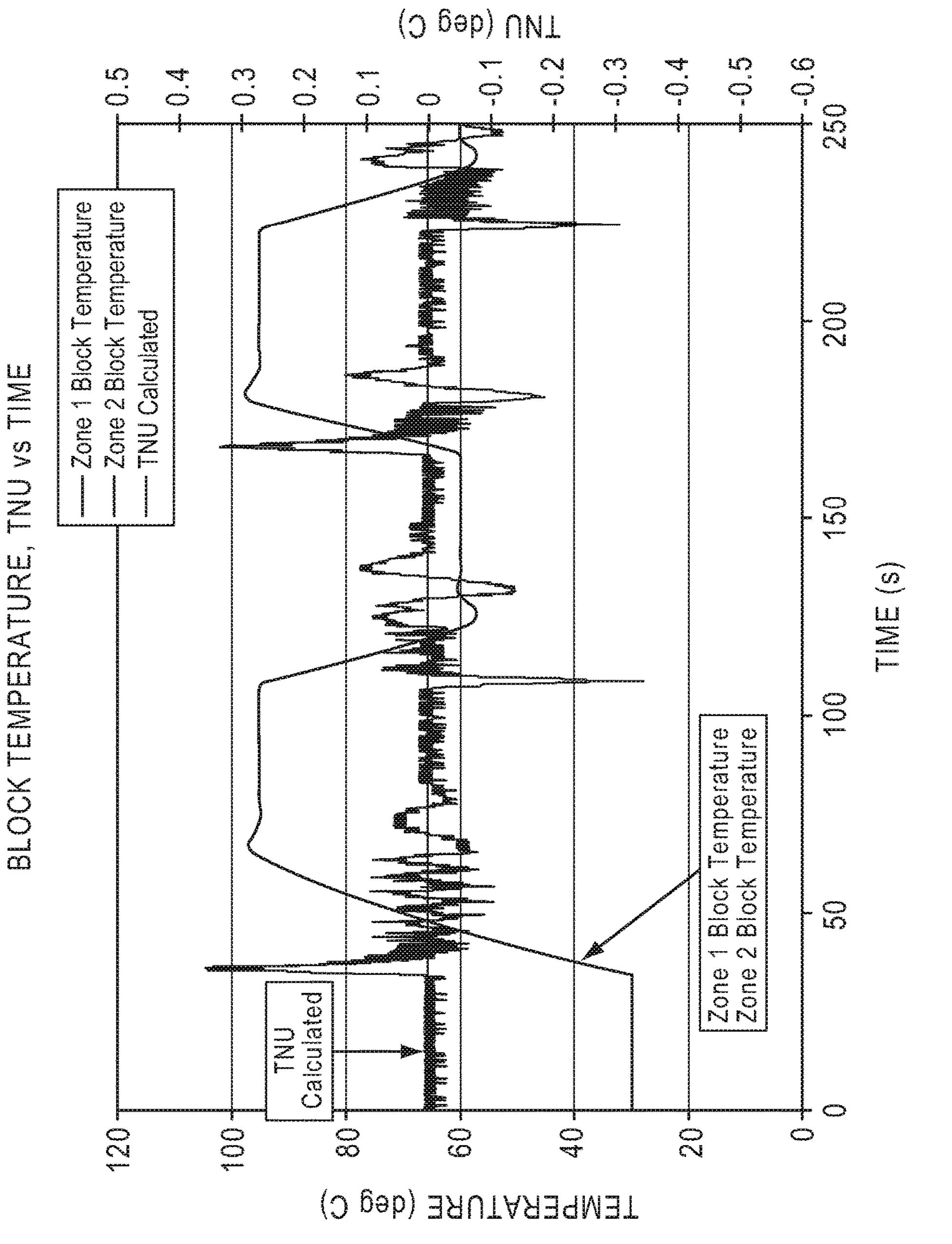
FIG. 21 is a graph illustrating a two PID controller system with a distributed system controller within the PID controllers.

FIG. 20 and FIG. 21 illustrate data collected before and after BSTD control implemented. FIG. 20 is a graph illustrating a two PID controller system without a distributed system controller. FIG. 21 is a graph illustrating a two PID controller system with a distributed system controller within the PID controllers. The thermal non uniformity (TNU) calculated in the graphs is obtained using the difference of the two thermal sample sector temperatures divided by 2. This TNU calculated correlates to actual TNU as the block sensor temperature represent the temperature of the block around thermal control region.

Figure 22:
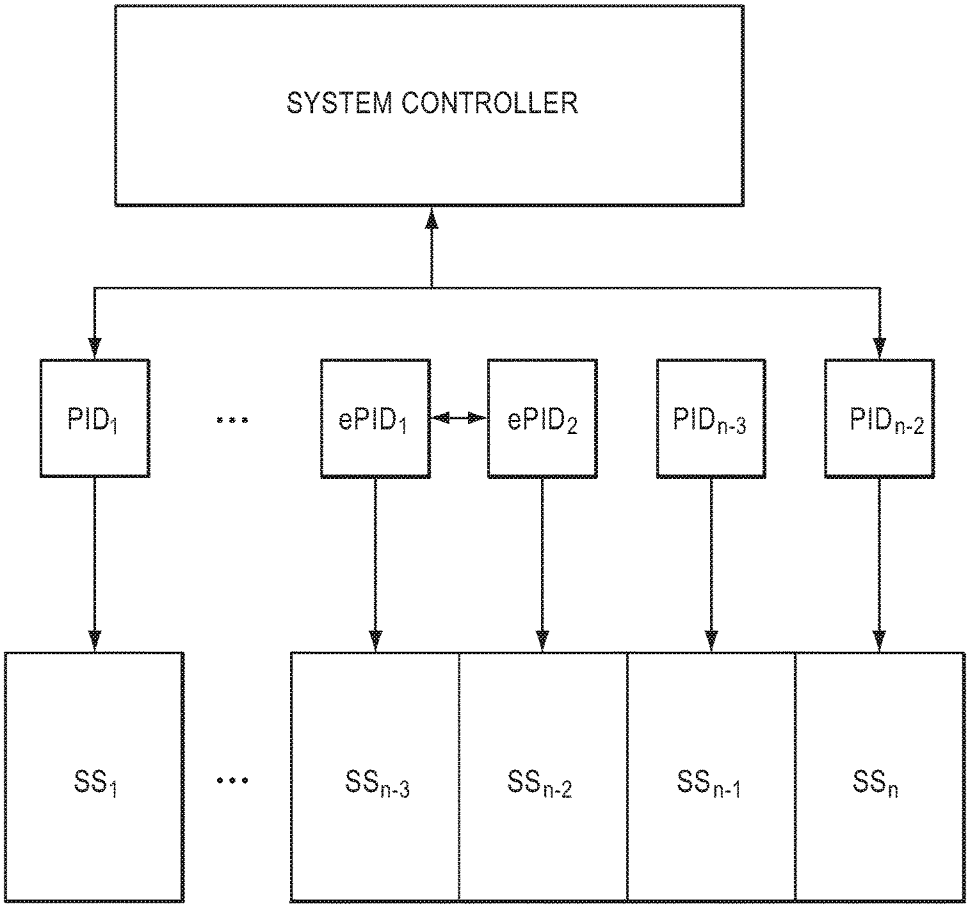
FIG. 22 illustrates a schematic representation where the system controller may also be a combination of the master system controller and the distributed system controller.

FIG. 22 illustrates a schematic representation where the system controller may also be a combination of the master system controller and the distributed system controller. The master system controller is in bidirectional communication with at least two of the PID controllers. Distributed system control is provided by at least two enhanced PID controllers. Each PID controller and enhanced PID controller is connected to a respective sample block sector.

Figure 23:
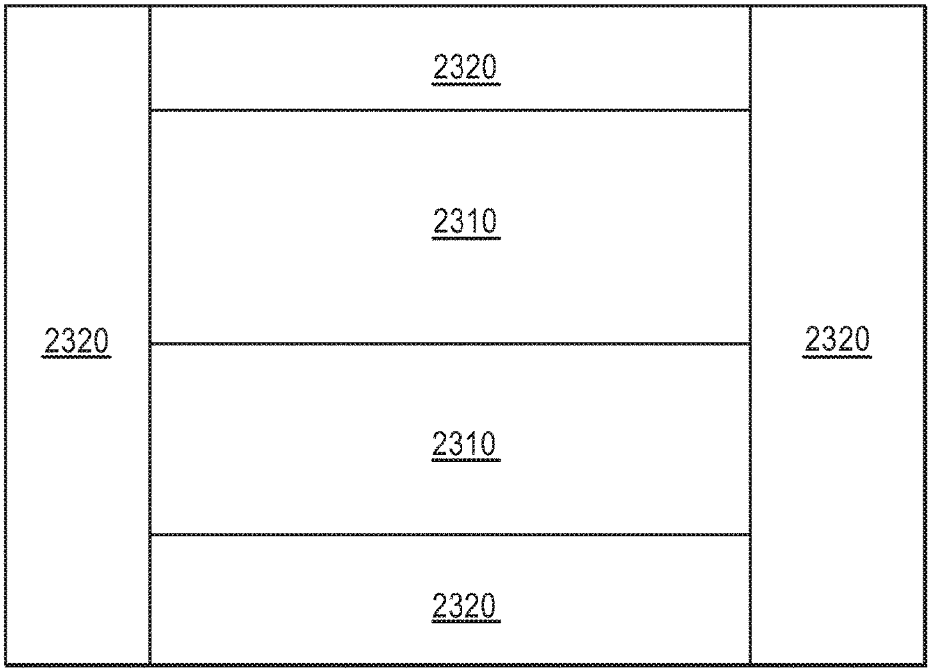
FIG. 23 illustrates a schematic representation of sample block sector array used in FIG. 22.

FIG. 23 illustrates a schematic representation of sample block sector array 2300 used in FIG. 22. The enhanced PID controllers control the temperature of the interior sample block sectors 2310. The master system controller controls the temperature of the exterior sample block sectors 2320.

Figure 24:
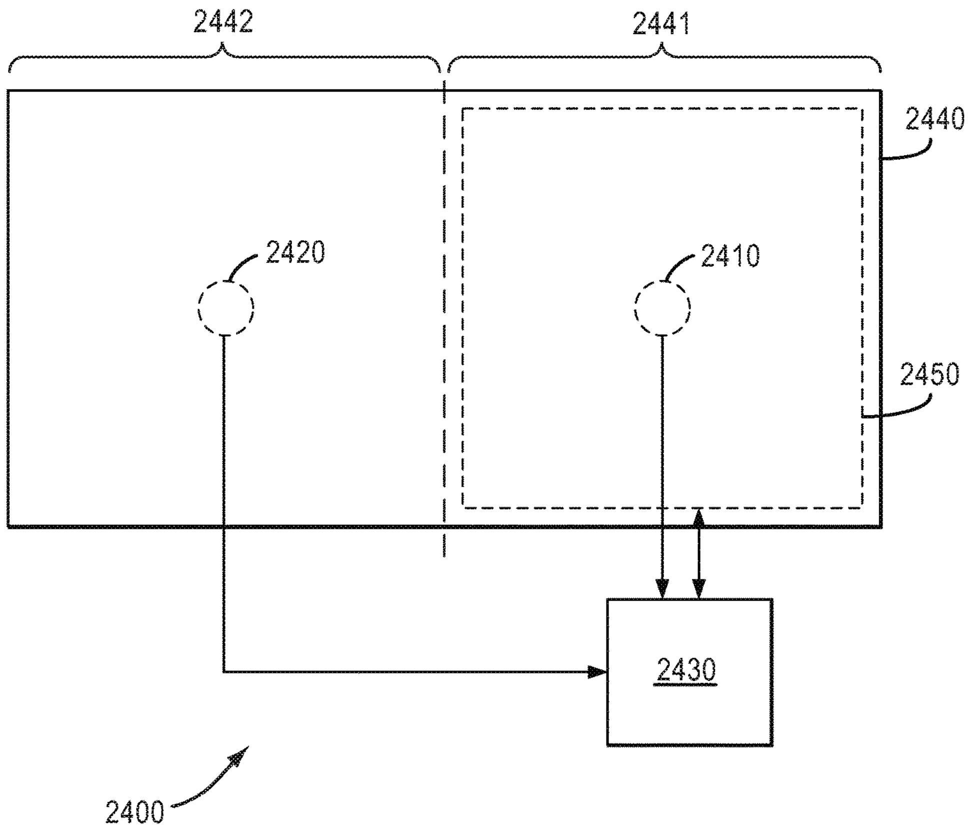
FIG. 24 is a diagram of a system for improving the thermal nonuniformity of a sample block of a PCR instrument, upon which embodiments of the present teachings may be implemented.

FIG. 24 is a diagram of a system 2400 for improving the thermal nonuniformity of a sample block of a PCR instrument, upon which embodiments of the present teachings may be implemented. System 2400 includes a first sensor 2410, a second sensor 2420, and a thermoelectric controller 2430. First sensor 2410 senses a first temperature of first sample block sector 2441 of sample block 2440. Second sensor 2420 senses a second temperature of second sample block sector 2442 of sample block 2440. Sample block sector 2441 is adjacent to sample block sector 2442.

Thermoelectric controller 2430 is in electrical communication with first sensor 2410, second sensor 2420, and one or more TECs 2450 used to heat or cool first sample block sector 2441. Thermoelectric controller 2430 reads the first temperature from first sensor 2410 and the second temperature from second sensor 2420. Thermoelectric controller 2430 calculates a difference in temperature between the first temperature and the second temperature. Finally, thermoelectric controller 2430 adjusts the power output to one or more TECs 2450 based on the difference in temperature.

In various embodiments, thermoelectric controller 2430 calculates the difference in temperature by subtracting the second temperature from the first temperature.

In various embodiments, thermoelectric controller 2430 reads the first temperature from first sensor 2410 and the second temperature from second sensor 2420 during a ramping up or ramping down of the power output to one or more TECs 2450.

In various embodiments, thermoelectric controller 2430 adjusts the power output of one or more TECs 2450 based on a ramp rate at which the power output to one or more TECs 2450 is ramping up or ramping down in addition to the difference in temperature.

Figure 25:
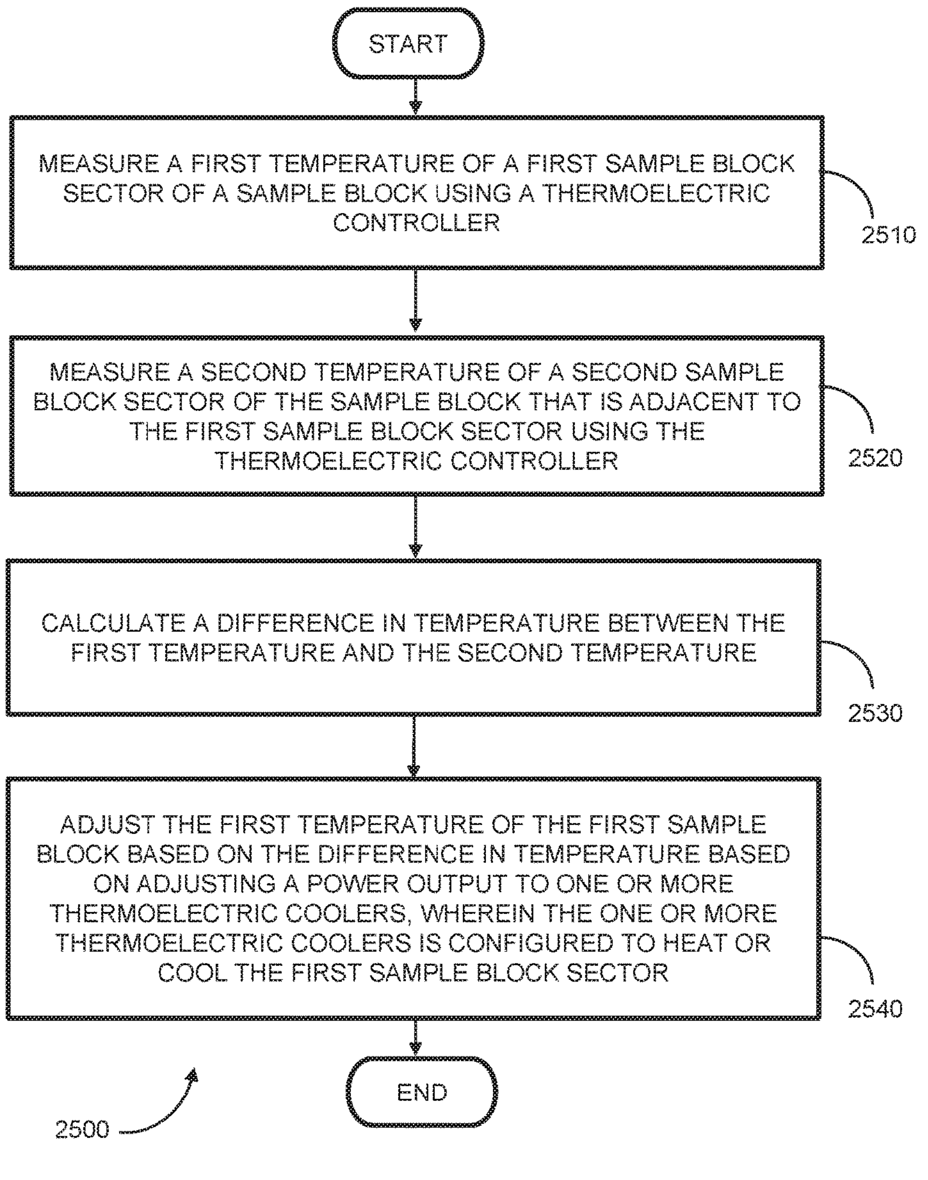
FIG. 25 is an exemplary flowchart showing a method for improving the thermal nonuniformity of a sample block of a PCR instrument, upon which embodiments of the present teachings may be implemented.

FIG. 25 is an exemplary flowchart showing a method 2500 for improving the thermal nonuniformity of a sample block of a PCR instrument, upon which embodiments of the present teachings may be implemented.

In step 2510 of method 2500, a first sensor is read that senses a first temperature of a first sample block sector of a sample block using a thermoelectric controller.

In step 2520, a second sensor is read that senses a second temperature of a second sample block sector of the sample block that is adjacent to the first sample block sector using the thermoelectric controller.

In step 2530, a difference in temperature is calculated between the first temperature and the second temperature using the thermoelectric controller.

In step 2540, the power output is adjusted to one or more TECs used to heat or cool the first sample block sector based on the difference in temperature using the thermoelectric controller.

In various embodiments, a tangible computer-readable storage medium is encoded with instructions, executable by a processor of a thermoelectric controller, so as to perform a method for improving the thermal nonuniformity of a sample block of a PCR instrument. This method is performed by a system of distinct software modules.

Figure 26:
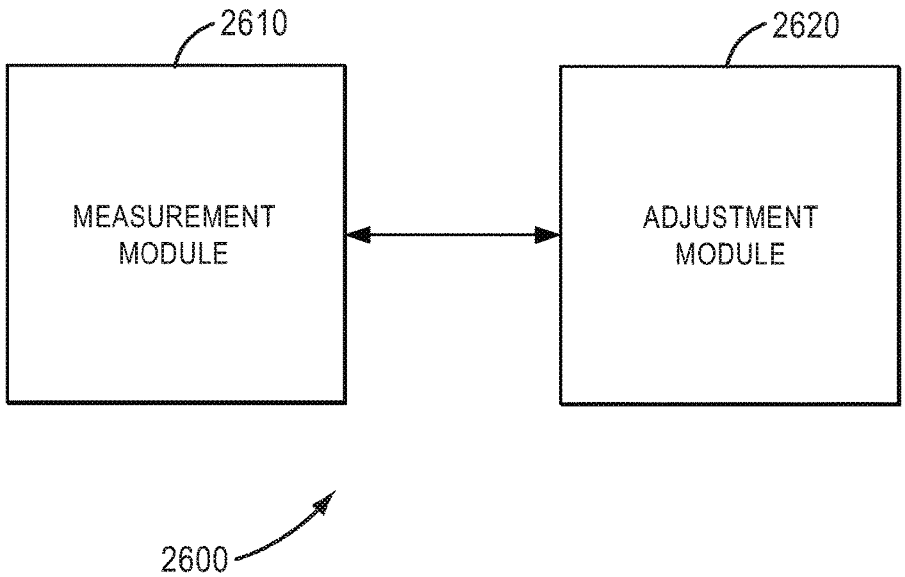
FIG. 26 is a schematic diagram of a system of distinct software modules that performs a method for improving the thermal nonuniformity of a sample block of a PCR instrument, upon which embodiments of the present teachings may be implemented.

FIG. 26 is a schematic diagram of a system 2600 of distinct software modules that performs a method for improving the thermal nonuniformity of a sample block of a PCR instrument, upon which embodiments of the present teachings may be implemented. System 2600 includes measurement module 2610, and adjustment module 2620.

Measurement module 2610 reads a first sensor that senses a first temperature of a first sample block sector of a sample block. Measurement module 2610 reads a second sensor that senses a second temperature of a second sample block sector of the sample block that is adjacent to the first sample block sector.

Adjustment module 2620 calculates a difference in temperature between the first temperature and the second temperature and adjusts a power output to the one or more TECs used to heat or cool the first sample block sector based on the difference in temperature.

Figure 27:
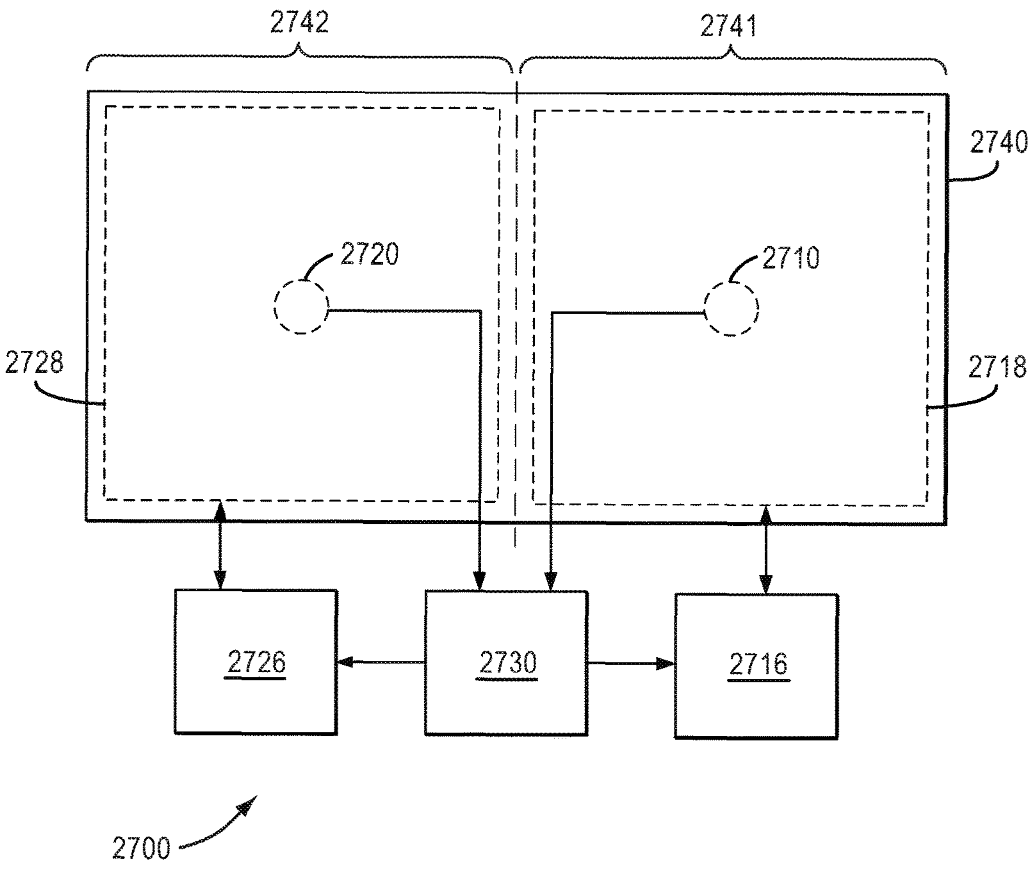
FIG. 27 is a diagram of a system for improving the thermal nonuniformity of a sample block of a PCR instrument using a master thermoelectric controller, upon which embodiments of the present teachings may be implemented.

FIG. 27 is a diagram of a system 2700 for improving the thermal nonuniformity of a sample block of a PCR instrument using master thermoelectric controller 2730, upon which embodiments of the present teachings may be implemented. System 2700 includes a first sensor 2710, a second sensor 2720, and master thermoelectric controller 2730. First sensor 2710 senses a first temperature of first sample block sector 2741 of sample block 2740. Second sensor 2720 senses a second temperature of second sample block sector 2742 of sample block 2740. Sample block sector 2741 is adjacent to sample block sector 2742.

First thermoelectric controller 2730 is in electrical communication with first sensor 2710, second sensor 2720, second thermoelectric controller 2716 that controls one or more TECs 2718 used to heat or cool first sample block sector 2741, third thermoelectric controller 2726 that controls one or more TECs 2728 used to heat or cool second sample block sector 2742. First thermoelectric controller 2730 reads the first temperature from first sensor 2710 and the second temperature from second sensor 2720. Thermoelectric controller 2730 calculates a difference in temperature between the first temperature and the second temperature. Finally, first thermoelectric controller 2730 instructs second thermoelectric controller 2716 to adjust its power output and the third thermoelectric controller 2726 to adjust its power output based on the difference in temperature.

In various embodiments, the functions of the master thermoelectric controller, first thermoelectric controller 2730, can be performed by either of the two slave thermoelectric controllers, second thermoelectric controller 2716, or third thermoelectric controller 2726.

Figure 28:
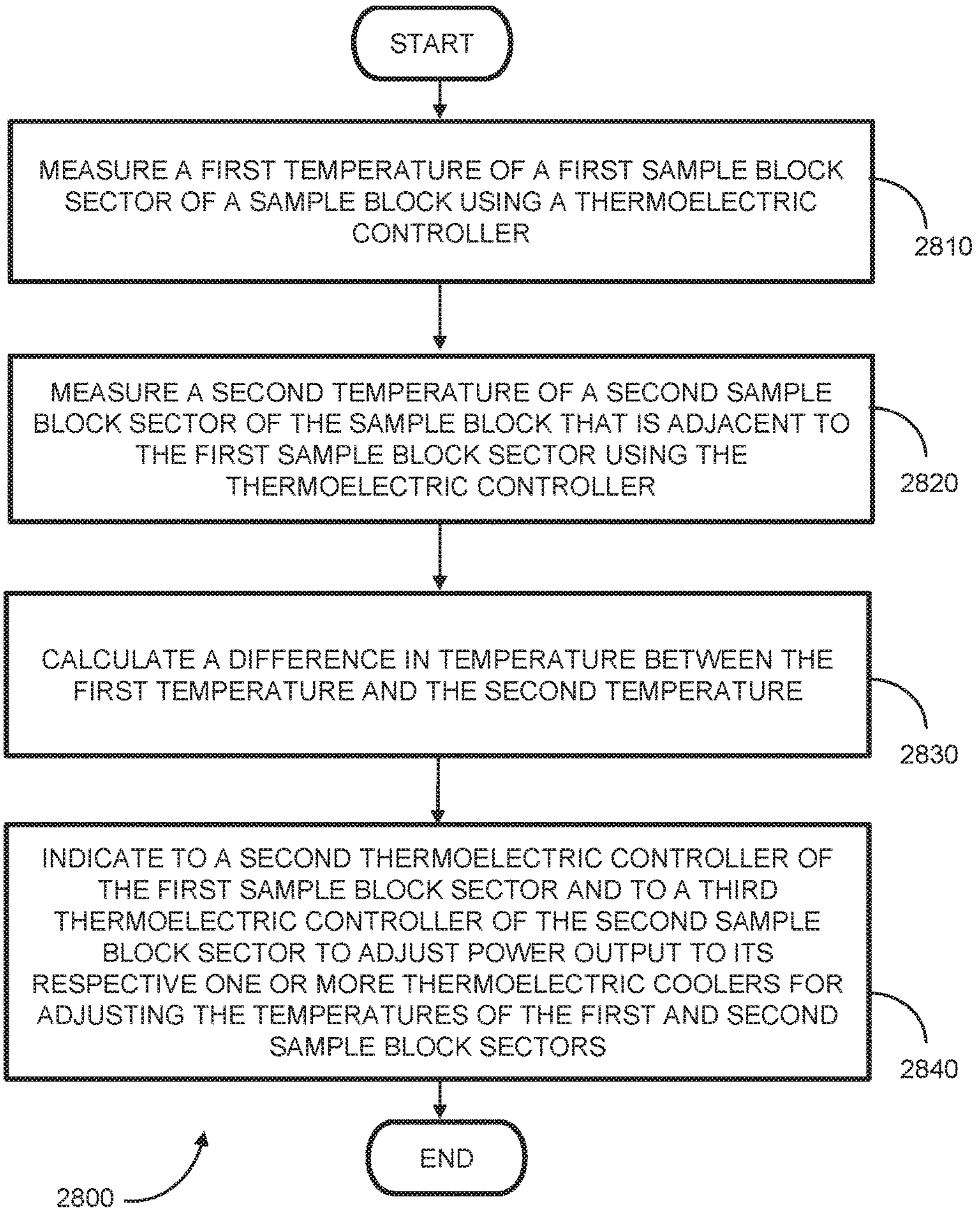
FIG. 28 is an exemplary flowchart showing a method for improving the thermal nonuniformity of a sample block of a PCR instrument using a master thermoelectric controller, upon which embodiments of the present teachings may be implemented.

FIG. 28 is an exemplary flowchart showing a method 2800 for improving the thermal nonuniformity of a sample block of a PCR instrument using a master thermoelectric controller, upon which embodiments of the present teachings may be implemented.

In step 2810 of method 2800, a first sensor is read that senses a first temperature of a first sample block sector of a sample block using a first thermoelectric controller.

In step 2820, a second sensor is read that senses a second temperature of a second sample block sector of the sample block that is adjacent to the first sample block sector using the first thermoelectric controller.

In step 2830, a difference in temperature is calculated between the first temperature and the second temperature using the first thermoelectric controller.

In step 2840, a second thermoelectric controller that controls one or more thermoelectric coolers used to heat or cool the first sample block sector adjusts its power output and a third thermoelectric controller that controls one or more thermoelectric coolers used to heat or cool the second sample block sector adjusts its power output based on the difference in temperature using the first thermoelectric controller.

In various embodiments, a tangible computer-readable storage medium is encoded with instructions, executable by a processor of a thermoelectric controller, so as to perform a method for improving the thermal nonuniformity of a sample block of a PCR instrument a master thermoelectric controller. This method is performed by a system of distinct software modules.

Figure 29:
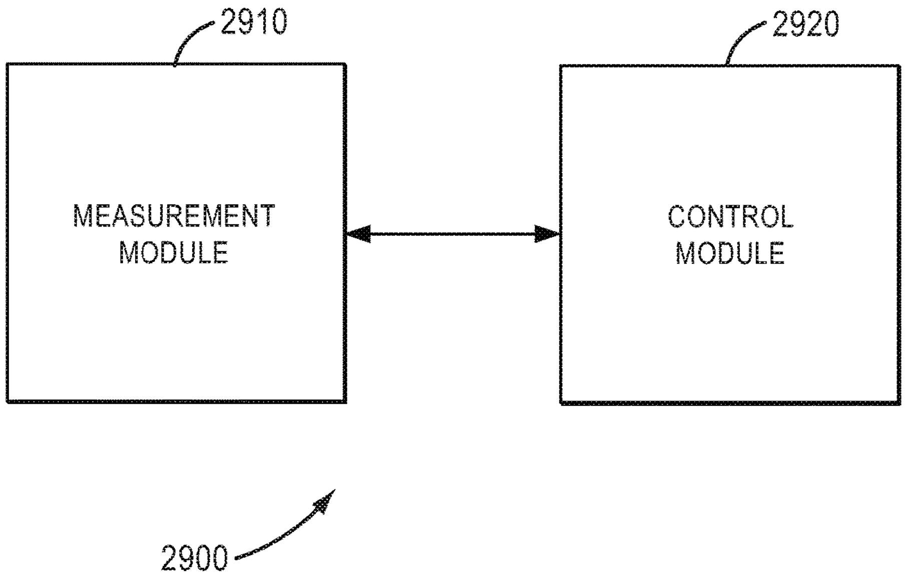
FIG. 29 is a schematic diagram of a system of distinct software modules that performs a method for improving the thermal nonuniformity of a sample block of a PCR instrument a master thermoelectric controller, upon which embodiments of the present teachings may be implemented.

FIG. 29 is a schematic diagram of a system 2900 of distinct software modules that performs a method for improving the thermal nonuniformity of a sample block of a PCR instrument a master thermoelectric controller, upon which embodiments of the present teachings may be implemented. System 2900 includes measurement module 2910, and control module 2920.

Measurement module 2910 reads a first sensor that senses a first temperature of a first sample block sector of a sample block. Measurement module 2910 reads a second sensor that senses a second temperature of a second sample block sector of the sample block that is adjacent to the first sample block sector.

Control module 2920 calculates a difference in temperature between the first temperature and the second temperature. Control module 2920 of a first thermoelectric controller that controls one or more thermoelectric coolers used to heat or cool the first sample block sector to adjust its power output and indicates to a second thermoelectric controller that controls one or more thermoelectric coolers used to heat or cool the second sample block sector to adjust its power output based on the difference in temperature.

While the principles of this invention have been described in connection with specific embodiments, it should be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

What is claimed is:

1. A method for performing polymerase chain reactions (PCR), the method comprising:

measuring a first temperature, by a first sensor, of a first sample block sector of a sample block;

measuring a second temperature, by a second sensor, of a second sample block sector of the sample block, wherein the second sample block sector is located adjacent to the first sample block sector;

calculating, by a controller, a difference in temperature between the first temperature and the second temperature; and adjusting, by the controller, the first temperature of the first sample block sector based on the difference in temperature to increase thermal uniformity across the first sample block sector and the second sample block sector during a PCR thermal protocol.

2. The method of claim 1, wherein the measuring of the first temperature by the first sensor and the second temperature from the second sensor occurs during a ramping up of the power output to a thermoelectric cooler.

3. The method of claim 1, wherein measuring the first temperature from the first sensor and the second temperature from the second sensor occurs during a ramping down of the power output to a thermoelectric cooler.

4. The method of claim 2, further comprising adjusting the power output to the thermoelectric cooler based on a rate at which the power output to the thermoelectric cooler is ramping up.

5. The method of claim 3, further comprising adjusting the power output to the thermoelectric cooler based on a rate at which the power output to the thermoelectric cooler is ramping down.

6. The method of claim 1, further comprising:

measuring a third temperature, by a third sensor, of a third sample block sector of the sample block;

calculating, by the controller, a difference in temperature between the third temperature and the first temperature and a difference between the third temperature and the second temperature; and adjusting, by the controller, the first temperature of the first sample block sector based on the difference between the first temperature and the second temperature, the difference between the third temperature and the first temperature, and the third temperature and the second temperature by adjusting the power output to the thermoelectric cooler.

7. The method of claim 1, further comprising:

adjusting, by the controller, the second temperature of the second sample block sector based on adjusting a power output to a second thermoelectric cooler, wherein the second thermoelectric cooler is configured to heat or cool the second sample block sector.

8. A computer-readable storage medium encoded with instructions, executable by a processor, for performing polymerase chain reactions (PCR), the instructions comprising instructions for:

measuring a first temperature of a first sample block sector of a sample block;

measuring a second temperature of a second sample block sector of the sample block, wherein the second sample block sector is adjacent to the first sample block sector;

calculating a difference in temperature between the first temperature and the second temperature; and adjusting the first temperature of the first sample block sector based on the difference in temperature to increase thermal uniformity across the first sample block sector and the second sample block sector during a PCR thermal protocol.

9. The computer-readable medium of claim 8, wherein measuring the first temperature and the second temperature occurs during a ramping up of the power output to a thermoelectric cooler using a controller.

10. The computer-readable medium of claim 8, wherein measuring the first temperature and the second temperature occurs during a ramping down of the power output to a thermoelectric cooler using a controller.

11. The computer-readable medium of claim 8, further comprising adjusting the power output to a thermoelectric cooler based on a rate at which the power output to the thermoelectric cooler.

12. The computer-readable medium of claim 9, further comprising adjusting the power output to the thermoelectric cooler based on a rate at which the power output to the thermoelectric cooler is ramping down.

13. The computer-readable medium of claim 9, wherein the instructions further include instructions for:

measuring a third temperature of a third sample block sector of the sample block;

calculating a difference in temperature between the third temperature and the first temperature and a difference between the third temperature and the second temperature; and adjusting the first temperature of the first sample block based on the difference between the first temperature and the second temperature, the difference between the third temperature and the first temperature, and the third temperature and the second temperature.

14. The computer-readable medium of claim 9, wherein the instructions further include instructions for:

adjusting the second temperature of the second sample block sector by adjusting a power output to a second thermoelectric cooler, wherein the second thermoelectric cooler is configured to heat or cool the second sample block sector.

15. A system for performing polymerase chain reactions (PCR), the system comprising:

a first sensor configured for detecting a first temperature of a first sample block sector of a sample block;

a second sensor configured for detecting a second temperature of a second sample block sector of the sample block, wherein the second sample block sector is adjacent to the first sample block sector; and a controller in electrical communication with the first sensor and the second sensor, wherein the controller is configured to:

receive the first temperature of the first sample block sector, receive the second temperature of the second sample block sector, calculate a difference in temperature between the first temperature and the second temperature, and adjust the first temperature of the first sample block sector based on the difference in temperature to increase thermal uniformity across the first sample block sector and the second sample block sector during a PCR thermal protocol.

16. The system of claim 15, wherein the controller receives the first temperature from the first sensor and the second temperature from the second sensor during a ramping up of the power output to a thermoelectric cooler.

17. The system of claim 15, wherein the controller receives the first temperature from the first sensor and the second temperature from the second sensor during a ramping down of the power output to a thermoelectric cooler.

18. The system of claim 16, wherein the controller adjusts the power output to the thermoelectric cooler based on a rate at which the power output to the thermoelectric cooler is ramping up in addition to the difference in temperature.

19. The system of claim 16, wherein the controller adjusts the power output of the thermoelectric cooler based on a rate at which the power output to the thermoelectric cooler is ramping down.

20. The system of claim 15, wherein the controller is further configured to:

adjust the second temperature of the second sample block sector based on adjusting a power output to a second thermoelectric cooler, wherein the second thermoelectric cooler is configured to heat or cool the second sample block sector.

* * * * *